(12) United States Patent
Shelley et al.

(10) Patent No.: US 8,012,554 B2
(45) Date of Patent: Sep. 6, 2011

(54) BAGS HAVING ODOR MANAGEMENT CAPABILITIES

(75) Inventors: Lindsay Shelley, Chicago, IL (US); Chieh-Chun Chau, Victor, NY (US); Wayne J. Moras, Chatham, IL (US); Harley E. Erb, IV, Lake Forest, IL (US)

(73) Assignee: Pactiv Corporation, Lake Forest, IL (US)

( * ) Notice: Subject to any disclaimer, the term of this patent is extended or adjusted under 35 U.S.C. 154(b) by 1028 days.

(21) Appl. No.: 11/854,418

(22) Filed: Sep. 12, 2007

(65) Prior Publication Data

US 2009/0067760 A1     Mar. 12, 2009

(51) Int. Cl.
*B29D 22/00* (2006.01)
*B29D 23/00* (2006.01)
*B32B 1/08* (2006.01)
*B32B 27/08* (2006.01)

(52) U.S. Cl. ............. 428/36.6; 428/35.2; 428/35.4; 428/35.7; 383/105; 206/524.3; 206/524.4; 424/401

(58) Field of Classification Search .......... 383/105; 206/524.3, 524.4; 428/35.2, 35.7, 35.4, 36.6; 424/401
See application file for complete search history.

(56) References Cited

U.S. PATENT DOCUMENTS

| 4,009,253 A | 2/1977 | Schleppnik et al. ............ 424/45 |
| 4,009,254 A | 2/1977 | Renold ............................ 424/59 |
| 4,171,340 A | 10/1979 | Nishimura et al. |
| 4,184,099 A | 1/1980 | Lindauer et al. |
| 4,187,251 A | 2/1980 | Schleppnik .................... 568/376 |
| 4,310,512 A | 1/1982 | Schleppnik |
| 4,348,455 A | 9/1982 | Clayton ......................... 428/336 |
| 4,430,457 A | 2/1984 | Dobreski ....................... 523/100 |
| 4,622,221 A | 11/1986 | Schleppnik .................. 424/76.4 |
| 4,624,991 A | 11/1986 | Haas .............................. 525/209 |
| 4,719,105 A | 1/1988 | Schleppnik ................ 424/76.21 |
| 4,735,803 A | 4/1988 | Katz et al. .................. 424/195.1 |
| 4,818,524 A | 4/1989 | Gibbs ........................... 424/76.1 |
| 4,837,421 A | 6/1989 | Luthy |
| 4,853,413 A | 8/1989 | Katz et al. ..................... 514/526 |

(Continued)

FOREIGN PATENT DOCUMENTS

CA     1041018     10/1978

(Continued)

OTHER PUBLICATIONS

"Innovation is Key!", A. Oberholz, Statement on the Occasion of Degussa Meets Science, Dec. 13/14, 2001, Düsseldorf, Germany, at http://www.degussa.com/degussa/MCMSbase/Pages/ProvideResource.aspx?respath=/NR/rdonlyres/DC1EC5.

(Continued)

*Primary Examiner* — Michael C Miggins
(74) *Attorney, Agent, or Firm* — Baker Botts LLP

(57) ABSTRACT

Bags or liners having incorporated therein an effective amount of odor management agents including a counteractant agent, a neutralizing agent and optionally, a masking agent, whereby the odor management agent imparts no perceptible scent to the bags or liners, such that the bags or liners are substantially free of fragrance while the odor management agent reduces malodor emanating from products disposed within the bag. Further, the invention is drawn to web materials for use in forming the bags or liners having odor management agents. The odor management agent is disposed within the bag or dispersed substantially uniformly throughout the web.

14 Claims, 20 Drawing Sheets

U.S. PATENT DOCUMENTS

| | | | |
|---|---|---|---|
| 4,968,496 A | 11/1990 | Roche et al. | |
| 5,067,208 A | 11/1991 | Herrington et al. | 24/400 |
| 5,174,462 A | 12/1992 | Hames | 220/87.1 |
| 5,275,496 A | 1/1994 | Fattori et al. | |
| 5,334,428 A | 8/1994 | Dobreski et al. | 428/34.9 |
| 5,348,667 A | 9/1994 | Bacon et al. | |
| 5,441,727 A | 8/1995 | Chatterjee et al. | 424/65 |
| 5,571,582 A | 11/1996 | Katoh | 428/35.5 |
| 5,593,670 A | 1/1997 | Trinh et al. | 424/76.1 |
| 5,652,206 A | 7/1997 | Bacon et al. | |
| 5,668,097 A | 9/1997 | Trinh et al. | 510/293 |
| 5,714,127 A | 2/1998 | DeWitt et al. | 422/131 |
| 5,762,971 A | 6/1998 | Schirmer | 425/133.1 |
| 5,783,544 A | 7/1998 | Trinh et al. | 510/293 |
| 5,783,657 A | 7/1998 | Pavlin et al. | |
| 5,861,371 A | 1/1999 | Wilsch-Irrgang et al. | 510/504 |
| 5,879,694 A | 3/1999 | Morrison et al. | |
| 5,928,634 A | 7/1999 | Uick et al. | |
| 5,939,060 A | 8/1999 | Trinh et al. | 424/76.4 |
| 5,942,217 A | 8/1999 | Woo | 424/76.1 |
| 5,968,494 A | 10/1999 | Kukkala et al. | |
| 6,000,926 A | 12/1999 | Schirmer | 425/133.1 |
| 6,042,586 A | 3/2000 | Kawano et al. | 606/107 |
| 6,083,611 A | 7/2000 | Eichbauer et al. | 428/213 |
| 6,111,055 A | 8/2000 | Berger et al. | |
| 6,147,588 A | 11/2000 | Nakayama et al. | 338/21 |
| 6,197,288 B1 | 3/2001 | Mankoo | |
| 6,207,274 B1 | 3/2001 | Ferenc et al. | |
| 6,257,401 B1 | 7/2001 | Mangla et al. | 206/204 |
| 6,265,350 B1 | 7/2001 | Schnatterer et al. | |
| 6,268,466 B1 | 7/2001 | MacQueen et al. | |
| 6,291,580 B1 | 9/2001 | Kukkala et al. | |
| 6,294,186 B1 | 9/2001 | Beerse et al. | |
| 6,306,415 B1 | 10/2001 | Reifenrath | |
| 6,325,565 B1 | 12/2001 | Girardot et al. | |
| 6,349,857 B1 | 2/2002 | Lepsius et al. | 222/391 |
| 6,386,778 B1 | 5/2002 | Guay et al. | |
| 6,410,567 B1 | 6/2002 | Jori | |
| 6,413,595 B1 | 7/2002 | Schirmer | 264/171.27 |
| 6,432,891 B1 | 8/2002 | O'connor | |
| 6,432,981 B1 | 8/2002 | Finke et al. | 514/322 |
| 6,440,925 B1 | 8/2002 | Suazon et al. | |
| 6,444,614 B2 | 9/2002 | Dean | |
| 6,451,844 B1 | 9/2002 | Watkins et al. | |
| 6,465,404 B2 | 10/2002 | Scriven, II et al. | |
| 6,465,406 B1 | 10/2002 | Drapier et al. | |
| 6,465,410 B1 | 10/2002 | Bettiol et al. | |
| 6,468,521 B1 | 10/2002 | Pedersen et al. | |
| 6,468,555 B1 | 10/2002 | Nakamura | |
| 6,469,131 B2 | 10/2002 | Lawson et al. | |
| 6,471,974 B1 | 10/2002 | Rees et al. | |
| 6,472,361 B1 | 10/2002 | Leonard et al. | |
| 6,475,505 B1 | 11/2002 | Stadler | |
| 6,475,526 B1 | 11/2002 | Smith | |
| 6,475,536 B2 | 11/2002 | Bombardelli et al. | |
| 6,475,537 B1 | 11/2002 | King et al. | |
| 6,475,976 B1 | 11/2002 | Mahieu et al. | |
| 6,478,440 B1 | 11/2002 | Jaworski et al. | |
| 6,479,039 B1 | 11/2002 | Dyer et al. | |
| 6,479,042 B1 | 11/2002 | Nguyen et al. | |
| 6,479,043 B1 | 11/2002 | Tietjen et al. | |
| 6,479,044 B1 | 11/2002 | Mahieu et al. | |
| 6,479,059 B2 | 11/2002 | Montanari et al. | |
| 6,479,444 B1 | 11/2002 | Porticos et al. | |
| 6,479,449 B1 | 11/2002 | Mondin | |
| 6,479,456 B1 | 11/2002 | Holzner | |
| 6,482,392 B1 | 11/2002 | Zhou et al. | |
| 6,482,423 B1 | 11/2002 | Beerse et al. | |
| 6,482,425 B1 | 11/2002 | Huet et al. | |
| 6,482,787 B1 | 11/2002 | Panandiker et al. | |
| 6,485,713 B1 | 11/2002 | Bonda et al. | |
| 6,485,736 B1 | 11/2002 | Shirley et al. | |
| 6,488,943 B1 | 12/2002 | Beerse et al. | |
| 6,488,948 B1 | 12/2002 | Danieli | |
| 6,488,949 B2 | 12/2002 | Shafer et al. | |
| 6,489,279 B2 | 12/2002 | Convents et al. | |
| 6,489,348 B1 | 12/2002 | Schelberger et al. | |
| 6,489,360 B2 | 12/2002 | Schelberger et al. | |
| 6,491,728 B2 | 12/2002 | Bacon et al. | |
| 6,491,840 B1 | 12/2002 | Frankenbach et al. | |
| 6,491,902 B2 | 12/2002 | Shefer et al. | |
| 6,491,933 B2 | 12/2002 | Lorenzi et al. | |
| 6,491,962 B2 | 12/2002 | Takaoka | |
| 6,492,313 B1 | 12/2002 | Connors et al. | |
| 6,495,124 B1 | 12/2002 | Samour | |
| 6,495,172 B1 | 12/2002 | France et al. | |
| 6,495,492 B1 | 12/2002 | Schallner et al. | |
| 6,495,499 B1 | 12/2002 | Puckhaber et al. | |
| 6,495,510 B1 | 12/2002 | Ofosu-Asante | |
| 6,495,512 B1 | 12/2002 | White et al. | |
| 6,495,575 B2 | 12/2002 | Dehne et al. | |
| 6,497,860 B1 | 12/2002 | Kawato et al. | |
| 6,498,133 B2 | 12/2002 | Borchers et al. | |
| 6,500,222 B2 | 12/2002 | Von Locquenghien et al. | |
| 6,503,488 B1 | 1/2003 | Rosen et al. | |
| 6,517,759 B1 | 2/2003 | Ferenc et al. | |
| 6,528,013 B1 | 3/2003 | Trinh et al. | |
| 6,528,047 B2 | 3/2003 | Arif et al. | 424/76.1 |
| 6,531,142 B1 | 3/2003 | Rabe et al. | |
| 6,531,444 B1 | 3/2003 | Shefer et al. | |
| 6,552,160 B2 | 4/2003 | Pavlin et al. | |
| 6,592,813 B1 | 7/2003 | Fox et al. | 422/5 |
| 6,610,648 B2 | 8/2003 | McGee | 512/21 |
| 6,613,338 B1 | 9/2003 | Schreiber et al. | |
| 6,644,494 B2 | 11/2003 | Hayes et al. | 220/839 |
| 6,703,011 B2 | 3/2004 | Shefer et al. | 424/76.4 |
| RE38,658 E | 11/2004 | Eichbauer | 428/343 |
| 6,845,878 B2 | 1/2005 | Hayes | 220/839 |
| 6,921,581 B2 | 7/2005 | Van Gelder et al. | 428/523 |
| 6,926,862 B2 | 8/2005 | Fontenot et al. | 422/5 |
| 2001/0002962 A1 | 6/2001 | Baines et al. | |
| 2003/0007945 A1 | 1/2003 | Arif et al. | |
| 2003/0110682 A1 | 6/2003 | Williams et al. | |
| 2003/0114323 A1 | 6/2003 | Booker et al. | |
| 2003/0199402 A1 | 10/2003 | Triplett et al. | |
| 2003/0223657 A1 | 12/2003 | Belias et al. | 383/105 |
| 2004/0066985 A1 | 4/2004 | Patel et al. | 383/64 |
| 2004/0074902 A1 | 4/2004 | Hayes et al. | 220/4.21 |
| 2004/0197505 A1 | 10/2004 | Jester et al. | 428/35.7 |
| 2005/0000966 A1 | 1/2005 | Nordland | 220/367.1 |
| 2005/0106192 A1* | 5/2005 | Parekh et al. | 424/401 |
| 2006/0291756 A1 | 12/2006 | Thomas | |

FOREIGN PATENT DOCUMENTS

| | | |
|---|---|---|
| CA | 1102349 | 6/1981 |
| CA | 1107201 | 8/1981 |
| EP | 1167507 A | 1/2002 |
| EP | 1250938 A | 10/2002 |
| GB | 1545561 | 5/1979 |
| WO | WO 96/05358 | 2/1996 |
| WO | WO 03/072343 A | 9/2003 |
| WO | WO 2007/073542 A | 6/2007 |

OTHER PUBLICATIONS

Jacob, et al, "Psychometric Evaluation of Responses to Pleasant and Malodour Stimulation in Human Subjects; Adaptation, Dose Response and Gender Differences", Int.J.Psychophysiology, (2003).
The Correlation Between Physiological and Psychological Responses to Odor Stimulation in Human Subjects, Clinical Neurophysiology, 113, (2002) , 542-551.
A Primer of Psychophysiology, James Hassett, Chapter 9 : The Brain.
US 6,492,318, 12/2002, Suazon et al. (withdrawn)

* cited by examiner

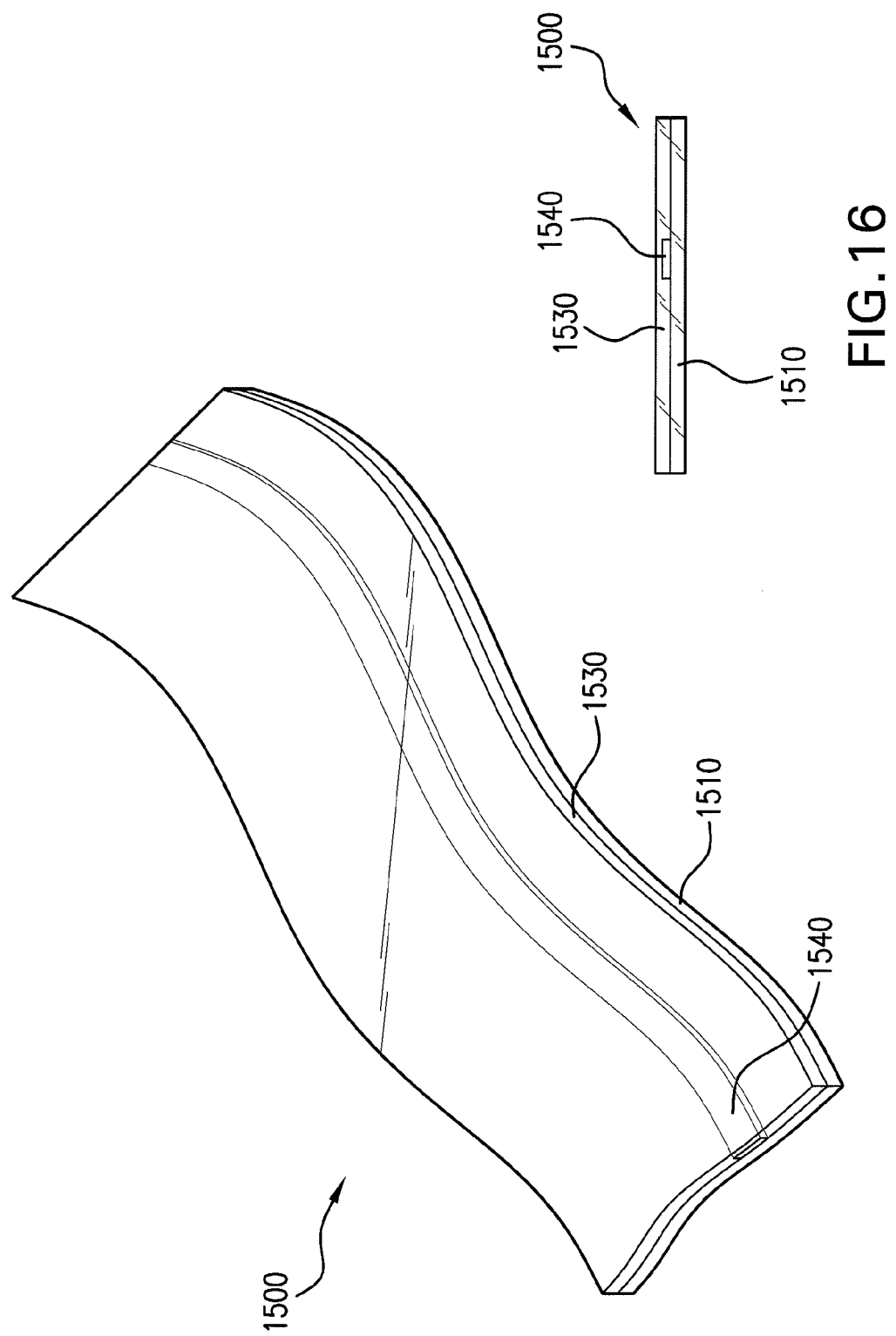

BAGS HAVING ODOR MANAGEMENT CAPABILITIES

FIELD OF THE INVENTION

The present invention relates to packages such as bags or liners having odor management capabilities. The present invention also relates to a web material, and more particularly to a web material for use in forming packages, and to structures and methods for releasing active agents in such packages. More specifically, the present invention relates to odor management agents and structures and methods for releasing such odor management agents to manage or control the odor related to such products disposed within such packages.

BACKGROUND OF THE INVENTION

The use of packages for a number of household and industrial purposes has gained wide acceptance. For example, bags or liners are commonly used in industrial settings and households to collect garbage or waste.

Waste that is collected in bags and liners can and often does produce unpleasant odors. Malodor can be generated from waste products and from degradation of waste during storage while waiting for removal from the premises. Waste malodor can be a nuisance and thus a method of managing malodor generation is highly desirable for home waste management. It is also desirable that the malodor from home waste can be reduced with a simple and cost effective method.

To address this problem, waste bag manufacturers have combined a scented resin (commonly termed "fragrance") with one or more polymeric resins during formation of such bags. This method is commonly referred to as "masking." U.S. Pat. No. 6,921,581, the content of which is incorporated herein in its entirety, discloses an example of the prior art that uses fragrances in the web to mask unpleasant malodor. The scented resin is therefore distributed uniformly throughout the bag. Such a scented waste bag assists in masking, neutralizing, and/or reducing at least some of the odors.

Scented waste bags can have a number of disadvantages. For instance, because the scented resin is distributed throughout the bag, the scent is not concentrated where a user is likely to encounter the unpleasant odors (e.g., the mouth of the bag). Further, manufacturing difficulties can arise from such bags. To obtain a desired amount of scent proximate the mouth of the bag, excess scent material may need to be distributed throughout the remainder of the bag, which can result in an overpowering scent that may be unpleasant to a user. However, if an insufficient amount of scent material is used, the scent provided may not be adequate to mask, neutralize, or reduce the malodor.

Additionally, because the scented resin used in such waste bags is likely to be more expensive than other polymeric resins used in forming the waste bags, it can be economically undesirable to distribute relatively equal amounts of scented resin throughout the bag. A need therefore exists for a package with a feature that manages odor without such disadvantages.

Furthermore, the scented formulation is commonly incorporated in the web in the melt extrusion of the bag and the scent is released over time. Masking scents usually possess certain characteristic fragrances to mask the malodor so that the fragrance, rather than the malodor, is primarily detected by the human olfactory system. This method achieves some positive odor reduction effect but is not desirable for many consumers due to the strong perception of the masking scent. The perception of scent is very subjective, so it is unlikely to find a scent that would fit all consumers' preferences. And, it is impractical to make products with many types of scent to fit individual customers' taste. Bags or liners with little or no perceptible scent constitute a popular and desirable demand. A method for making a bag or liner being substantially free of fragrance so as to have no perceptible scent but which still substantially reduces malodors from waste products disposed therein is therefore highly desirable. Web materials used to form the foregoing and other packages typically consist of extruded polymers. As used herein, the term "web" includes a variety of thin material structures, such as films, sheets and the like. Such web materials can be used in stock form for the manufacture of wrap or lidding materials. Alternatively, the web materials can be used in forming processes, such as thermoforming processes to form contoured containers, or heat sealing processes to form flexible containers, such as bags. In the case of wrap materials, a cling material or cling layer is typically desirable. In the case of lidding materials, materials that facilitate heat sealing or are otherwise capable of being adhered to another material, for example by way of an adhesive, are typically desirable.

SUMMARY OF THE INVENTION

The present invention provides for a bag having odor management capabilities. In particular, the present invention provides for bags or liners having an odor management agent incorporated therein in an amount such that the bags or liners are substantially free of fragrance so as to have no perceptible scent, but in a sufficient amount to substantially reduce malodors from waste products disposed therein. The present invention further provides for method of manufacturing the bags or liners of the invention. The invention is based on incorporating into a bag or liner of the invention an odor management agent that includes a counteractant, a neutralizing agent and, optionally, a masking agent, to reduce the perceived malodor from the waste product, but to impart no perceptible scent such that the bag is substantially free of fragrance.

In a particular embodiment, the present invention provides for a bag having odor management capabilities, the bag comprising a pair of opposing body panels joined together along a pair of opposing sides and a bottom bridging the sides; and an odor management agent distributed in at least one of the body panels for release into an interior of the bag to substantially reduce malodors emanating from products disposed within the bag, wherein the odor management agent comprises a counteractant, and wherein the bag is substantially free of fragrance.

The counteractant may be 1-cyclohexyl-1-ethyl formate, 1-cyclohexyl-1-ethyl acetate, 1-cyclohexyl-1-ethyl proprionate, 1-cyclohexyl-1-ethyl isobutyrate, 1-cyclohexyl-1-ethyl n-butyrate, 1-cyclohexyl-1-propyl acetate, 1-cyclohexyl-1-propyl n-butyrate, 1-cyclohexyl-2-methyl-1-propyl acetate, 2-cyclohexyl-2-propyl acetate, 2-cyclohexyl-2-propyl propionate, 2-cyclohexyl-2-propyl isobutyrate, 2-cyclohexyl-2-propyl n-butyrate, 1-cyclohexylethan-1-yl acetate, 1-cyclohexylethan-1-yl butyrate, 1-cyclohexylethan-1-ol, 1-(4'-methylethyl)cyclohexylethan-1-yl propionate, 2'-hydroxyl-1'-ethyl(2-phenoxy)acetate.

The odor management agent may further include a neutralizing agent, which may be a lauryl methacrylate, a biguanide, a quaternary ammonium compound, an ester of unsaturated monocarboxylic acid, an uncomplexed cyclodextrin, a zinc ricinoleate compound, and an alkoxylated amine having the formula $R(nAO)_xNH_t$, wherein R is a saturated or unsaturated, linear or branched alkyl containing from 8 to 22 carbon atoms, AO is a $C_2$-$C_6$ alkoxylate, n is the number of moles of AO and is from 1 to 50, s is 1, 2 or 3, t is 0, 1 or 2, and the sum of s and t is 3.

The present invention further provides for a method of forming a bag having odor management capabilities, which method comprises: providing a masterbatch including an odor management agent, the odor management agent comprising a counteractant; providing a matrix polymer; mixing and melting the masterbatch with the matrix polymer to form a molten polymer mixture, and extruding the molten polymer mixture through at least one extruder to create a web; and forming the web into a bag having a pair of body panels joined along opposing sides and along a bottom bridging the sides, the odor management agent distributed in at least one of the body panels for release into an interior of the bag to substantially reduce malodors emanating from products disposed within the bag, wherein the bag is substantially free of fragrance.

The present invention also provides for a bag having odor management capabilities, the bag comprising a pair of opposing body panels joined together along a pair of opposing sides and a bottom bridging the sides; and an odor management agent associated with at least one of the body panels for release into an interior of the bag to substantially reduce malodors emanating from products disposed within the bag, wherein the odor management agent comprising a counteractant and a neutralizing agent, and wherein the bag is substantially free of fragrance.

In a particular aspect of the invention, the association is by being distributed in at least one of the body panels for release into an interior of the bag.

A key difference of this invention and the prior art is that the bags or liners manufactured according to the invention are substantially free of fragrance so as to have no perceptible scent yet the bags or liners substantially reduce the perception of malodors, so that the malodor reduction mechanism does not rely primarily on masking. For example, U.S. Pat. No. 6,703,011 represents an example of the prior art that uses fragrances in the film to mask unpleasant odor.

In accordance with the invention, a web material is provided having a first material layer made of a barrier material and an active agent carried by the first material layer. As used herein, the term "web" generally includes relatively thin material structures, such as a film, a sheet, or the like. In some aspects, as used herein, a "web" can be provided as a continuous sheet of material manufactured or undergoing manufacture, or a portion thereof, such as in the form of a panel or sheet. A web can range from between 0.2 mil and 100 mil in thickness. For use in flexible packages, such as bags, the thickness is preferably between 0.7 mil and 6 mil. For use in more rigid containers, the web thickness is preferably between 8 mil and 100 mil. For use as a wrap material, the thickness is preferably between 0.5 mil and 1.5 mil, and for use as a lidding material, the thickness is preferably between 1 mil and 15 mil. As used herein, 1 mil is equal to $1/1000$ inch.

Preferably, the barrier material of the first layer is capable of inhibiting the transfer of water and/or active agent therethrough. Embodied as such, the barrier material is preferably capable of inhibiting transfer of solid, liquid and gas forms of water and active agent. Generally, barrier materials that demonstrate resistance to oxygen diffusion also demonstrate resistance to the diffusion of active agent vapor therethrough.

The active agent can be disposed on the first material layer, such as in a coating applied thereto, or can be impregnated or otherwise incorporated into the first material layer. If the active agent is disposed in the form of a coating on the first material layer, the coating can be formed or applied by a spray, by dipping the first material layer into active agent, through static adhesion, printing, co-extrusion, electroless deposition, casting, vapor deposition, fusion, and/or embedding processes. Printing can include any suitable method, such as with printing plates, roller, brush, or ink jet.

In accordance with a further aspect of the invention, the active agent can be disposed in the form of a stripe or pattern on the first material layer. The stripe can be applied as coating, co-extruded with the first material layer, or applied as a separate layer. The pattern can include a logo, stripes, cross-hatch pattern, dots or the like. The pattern can extend essentially across an entire surface of the first material layer, or can be applied only to a predetermined area, which itself can be in the form of a stripe or band.

If the active agent is incorporated in the web material, any of a variety of suitable techniques can be used. For example, the active agent can be disposed in microcapsules, or through co-extrusion with the barrier material of the first material layer.

The active agent can be selected, for example, from antimicrobial agents, odor management agents, fragrants, and combinations thereof. A preferred active agent is an odor management agent.

Web materials, in accordance with the invention, can include a second material layer having a predetermined material property. Such material properties can include cling characteristics and/or sealing characteristics. Such characteristics can be imparted by way of forming the second layer of the web material from one or more suitable materials.

Additionally or alternatively, the second material layer can be permeable to the active agent and/or water, and can be hydrophilic. In this manner, the active agent can be disposed in an intermediate layer between the first material layer and the second material layer. Release and/or production of active agent can be affected by the introduction of water.

Alternatively, the second material layer can be made of a barrier material, and can be removable from the first material layer. Also, in accordance with the invention, the web material can be disposed in a roll.

The web material of the invention can form a lidding material or a wrap material, based on the material provided for the first layer. Alternatively, the web material can be formed into a package or at least a body panel thereof. For example, certain packages include a pair of opposing body panels joined together along a pair of opposing sides and a bottom bridging the sides, a reclosable fastener extending along a mouth formed opposite the bottom, and at least one active agent. Certain other packages disclosed herein are rigid or semi-rigid molded containers where a film lid or over wrap has been applied thereto, while in other embodiments, packages are wrap materials, such as food wrap, that are used to cover perishable items.

In accordance with one aspect of the invention, a bag is provided that includes a pair of opposing body panels, wherein at least one of the body panels is formed of a web. The pair of opposing body panels are joined together along a pair of opposing sides and a bottom bridging the sides to define a compartment between the opposing body panels. The web, from which at least one of the body panels is formed, includes a first material layer made of a barrier material, and an active agent carried by the first material layer in communication with the compartment. A mouth can be defined between the pair of panels opposite the bottom, and active agent can be disposed in a stripe proximate the mouth. Further, any of the optional features set forth above can be incorporated into this aspect of the invention.

These and other features of the disclosed packages of the present invention can be more fully understood by referring to the following detailed description and accompanying drawings. The drawings are not drawn to scale, but show only relative dimensions.

BRIEF DESCRIPTION OF THE DRAWINGS

FIGS. 15 and 16 are isometric and end views, respectively, of another embodiment of a web material in accordance with the invention, including a stripe embedded between first and second layers of the web material;

DETAILED DESCRIPTION

Figure 1:
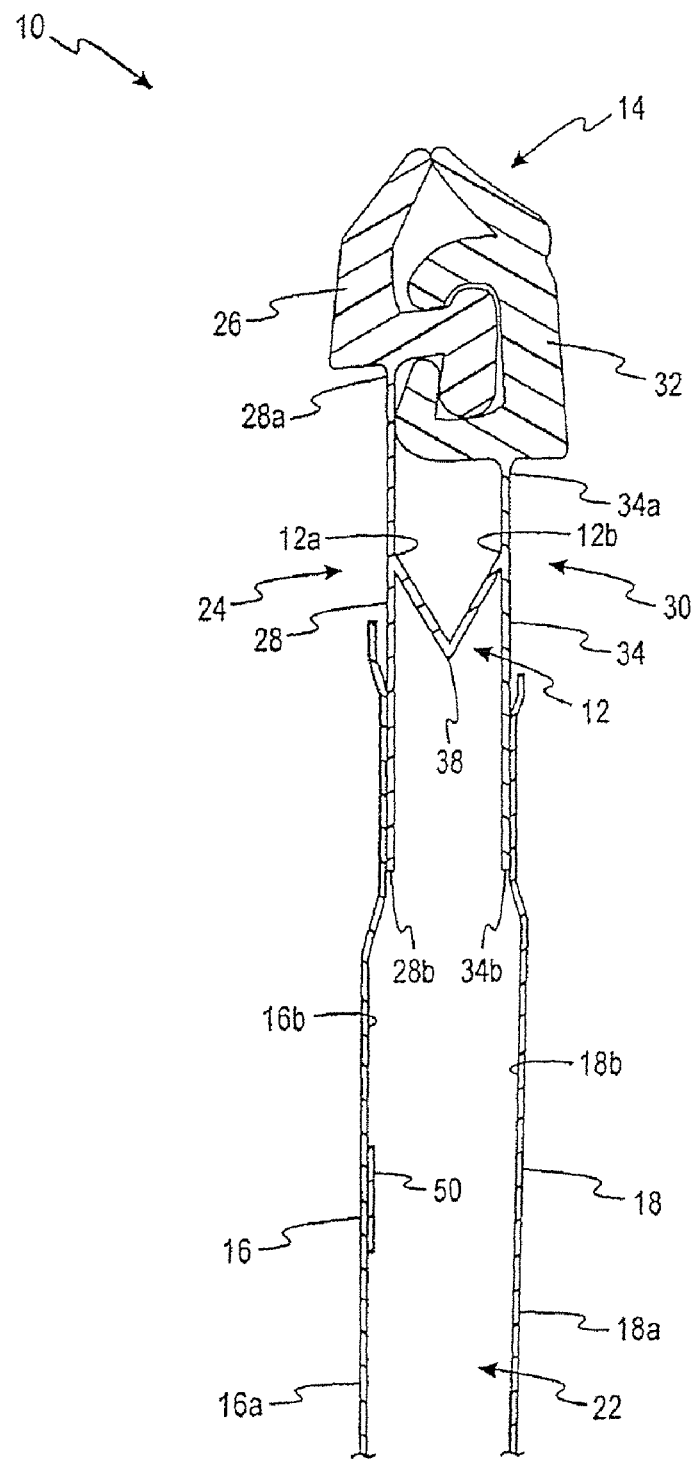
FIG. 1 is a sectional view of a mouth portion of a reclosable package or bag with the opposing body panels attached to respective fin portions according to one embodiment of the present invention.

The present invention relates to packages, packaging materials, materials for forming such packages and other related web materials having an active agent incorporated therein or carried thereon. As such, the invention has applications for various flexible and rigid containers and packages, such as reclosable plastic bags, waste bags and liners, rigid trash containers, air-tight storage containers, food containers, as well as wraps and foils commonly used for packaging, covering or sealing perishable items.

In accordance with one aspect of the invention, a web material is provided including a first layer of barrier material with an active agent carried thereon. In one embodiment, the barrier layer defines at least a portion of a body panel of a package. The active agent can be carried on the barrier layer in the form of a pouch, patch, tape or the like, or can otherwise be printed, coated, adhered to or incorporated, impregnated or disposed on the first layer. Various embodiments will be described for the purpose of illustration and not limitation.

As used herein, the term "package" can be understood to include any kind of package or container, such as flexible plastic bags and rigid containers, as well as foils, wraps or lidding materials commonly used to package or store perishable items.

As used herein, the term "active agent" can be understood to include any agent, ingredient, or composition that provides an enhancing or beneficial effect within a package or container. An active agent can include an "odor management" agent for masking, neutralizing and/or reducing odors from the package, or another functional agent. For example, an active agent can include an atmosphere modifier, e.g., a drying agent, a water absorbing agent, or a gas releasing agent; an enhancer, e.g., a flavor enhancer, or an agent that enhances any other function, such as water absorption, insulation, or microwave cooking; an inhibitor which inhibits or deters a certain condition, e.g., a spoilage inhibitor, a fungus inhibitor, a soil inhibitor, a flame inhibitor, a UV inhibitor, a freezer burn inhibitor, or an anti-static agent; or an indicator, e.g., an indicator of food ripeness or spoilage, or of contamination, temperature, moisture, modified atmosphere, or the presence of particular gas or a compound in the atmosphere, or the passage of time, e.g. timed release; or otherwise used or used in conjunction with such an indicator.

According to the present invention, the odor management agents used in an effective amount should impart no perceptible scent to the bags of the invention, so that the bags of the invention are substantially free of fragrance, while reducing malodors emanating from products disposed within the bags. The perceptible odor intensity of the film can be determined using ASTM E544-99 or a modified version of the test. The bags or liners and containers of the invention should be substantially free of fragrance so as to have no perceptible scent while reducing malodors, thus resulting in improved garbage malodor performance ratings from conventional garbage sniff tests. In the present invention, bags were produced that are substantially free of fragrance so as to have no perceptible scent, thus having an odor intensity closer to an unscented control bag than to a conventional scented bag while achieving a 50% reduction in the perception of malodor from the waste product disposed therein.

A further part of the invention is to provide a controlled delivery method of the odor management agents from the bag into the environment. A controlled delivery means is also useful in reducing the amount of the odor management agent to be consumed to achieve the same effectiveness, and preserve or protect the unscented formulation during filmmaking and storage. Controlled delivery can be achieved, for example, by incorporating the odor management agent in the form of a masterbatch, such as during an extrusion process for an extruded web which forms the panels of the bags or liners.

Additionally, the odor management agent is coextruded in one of a layer of a multiple layer web structure. Alternatively, the odor management agent may be added as a mineral additive such calcium carbonate or talc, in an extrusion web. If the odor management agent is added with a mineral additive, hydrophilic materials may optionally be added to the extrusion process.

Each of the active agents of the present invention can be used in combination with the web material and the packages formed with such web materials, as described below. For example, each odor management agent of the present invention can be used to reduce, neutralize, and/or mask odors from the package. Each of the active agents of the present invention can be carried by or otherwise disposed on the web material so as to be in communication with the environment of the package, e.g., disposed in the form of a coating, patch, pouch, or tape that is attached to a component of the package; extruded with a component of the package; sprayed, brushed, coated, laminated, or stamped onto a component of the package; impregnated into a component of the package; and/or distributed in the material of a component of the package, such as in the form of microcapsules. The active agents can also be carried by or disposed on a web material for use as, or as part of packages by printing, which can be achieved by printing plates, rollers, brushes, or ink jets, for example. The active agents can also be disposed by way of electroless deposition, vapor deposition, casting, fusion or embedding processes.

For purposes of illustration and not limitation, the web materials of the present invention can be used to form a polymeric bag for storing perishable items, with the active agent(s) in communication with the environment inside such polymeric bag. The polymeric bag can be intended for consumer storage of food products (e.g., leftover food products) or commercial applications, such as "fill, and seal" food packaging operations. The polymeric bag can include non-reclosable or reclosable polymeric bags. Reclosable polymeric bag are typically made to be reclosable via reclosable elements or fasteners, such as resealable adhesive or cohesive seals, mated tracks, and/or mated dimples. The mated tracks can be opened and closed by applying finger pressure or by using an auxiliary device, such as a slider. Some examples of reclosable polymeric bags include the bags disclosed in U.S. Pat. Nos. 5,067,208 and 6,147,588 and U.S. patent application Publication Ser. No. 2004/0066985, the contents of which documents are expressly incorporated by reference herein in their entireties. These packages are often manufactured from a web of material initially disposed in roll form prior to forming of individual bags.

Further for purposes of illustration and not limitation, the active agents of the present invention can also be disposed in the environment of a rigid package for storing perishables, such as bakery containers, deli containers, fruit containers, lunch containers, processing trays, such as those for poultry or ground meat, and roaster containers. Some examples of containers include containers disclosed in U.S. Pat. Nos. 6,042,586, 6,257,401, 6,349,857, 6,644,494, 6,845,878 and U.S. patent application Publication Ser. Nos. 2004/0074902 and 2005/0000966, the contents of which documents are expressly incorporated by reference herein in their entireties. These can be are either of a "clam-shell" type, having a hinged lid or can be covered with a web material such as a film overwrap or lidding material. Such overwrap and lidding materials can be provided in the form of a web. The film overwrap preferably includes a cling layer, such that the film overwrap can be used to wrap the entire package. If lidding material is provided, a processing machine or "lidding machine" can be used to seal the lidding material to the rigid package. Such sealing is typically effected by virtue of heat sealing and the preselected material properties, but can also include the use of an adhesive.

For purposes of illustration and not limitation, the odor management agents of the present invention can be used in the environment of bags, liners and rigid trash containers for collecting garbage or waste and other containers for collecting items with undesirable odors, such as laundry and diapers. Such waste bags can include a tie feature that assists in closing the bag or liner securely, forming a handle for carrying the bag or liner to be disposed, and/or facilitating the opening of the bag or the liner. Some examples of waste bags include the bags disclosed in U.S. patent application Publication Ser. No. 2003/0223657, the contents of which document is expressly incorporated by reference herein in its entirety.

Illustrative embodiments will now be described to provide an overall understanding of the disclosed packages and related web materials and active agents. For purposes of illustration and not limitation, the packages of the present invention are described in the context of reclosable polymeric bags made from the subject web materials having active agent. Illustrative embodiments are provided in the drawings. Those of ordinary skill in the art will understand that each disclosed web material, package and/or bag having an active agent can be adapted and modified to provide alternative embodiments for other applications, and that other additions and modifications can be made to the disclosed web materials, packages and active agents without departing from the scope of the present disclosure. For example, features of the illustrative embodiments can be combined, separated, interchanged, and/or rearranged to generate other embodiments. Such modifications and variations are intended to be included within the scope of the present disclosure.

Figure 2:
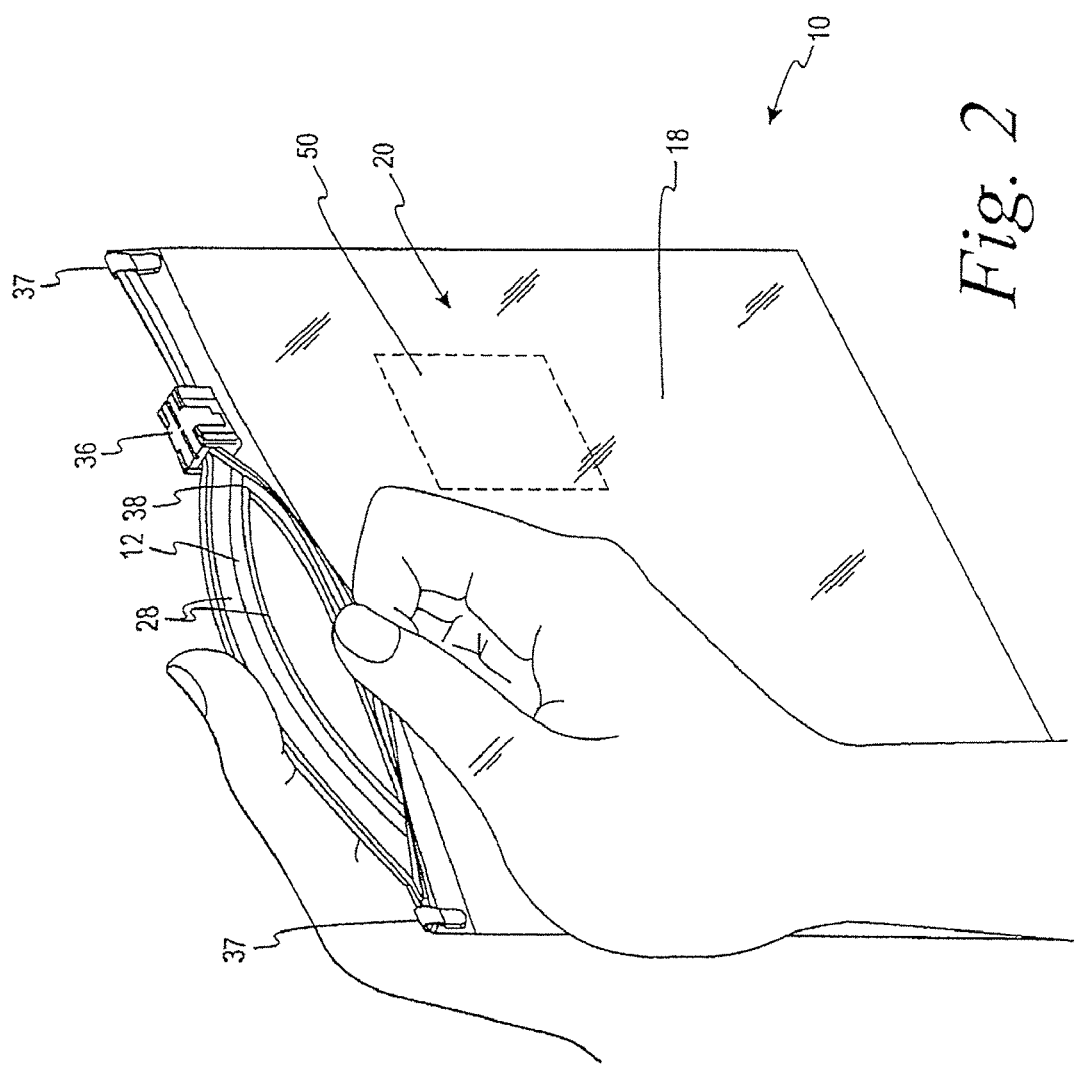
FIG. 2 is a perspective view of the reclosable package incorporating the mouth portion depicted in FIG. 1 in which the reclosable fastener or zipper has a slider mechanism being opened and the one-time breakable element being partially opened according to another embodiment.

Turning now to the drawings, FIG. 1 depicts a mouth portion of a reclosable package 10 with an agent structure 50 containing an active agent. The agent structure 50 is located below a reclosable closure arrangement such as a fastener or zipper 14. FIG. 2 shows the reclosable package 10 with the mouth portion depicted in FIG. 1 in a partial open position.

Referring to FIGS. 1 and 2, the mouth portion of the reclosable package 10 includes a pair of first and second opposing body or wall panels 16, 18 that make up a package body 20 and define an interior space 22. Typically, the body or wall panels 16, 18 are formed from a web of stock material. The web can be provided certain features prior to forming into the body or wall panels. The web of material can be provided with any of the active agents set forth herein, prior to forming the reclosable package 10. Connected to the first body panel 16 is a first track 24 having a first profile 26 and a first fin portion 28 extending generally downward from the first profile 26. The first body panel 16 has an outer surface 16a and an inner surface 16b. Connected to the second body panel 18 is a second track 30 having a second profile 32 and a second fin portion 34 extending generally downward from the second profile 32. The second body panel 18 has an outer surface 18a and an inner surface 18b. The inner surface 16b is attached to the first fin portion 28. The inner surface 18b is attached to the second fin portion 34. It is contemplated that one or more of the fin portions can be attached to the outer surfaces 16a, 18a.

The first and second profiles 26, 32 are releasably engageable with each other to provide a reclosable seal to the package 10. An optional breakable element 12 that initially extends from the first fin portion 28 to the second fin portion 34 can be used. The breakable element 12 of FIG. 1 is depicted with an optional one-time breakable preferential area of weakness or preferential tear area 38 to form a one-time breakable tamper evident feature. It is not necessary that the breakable element 12 have the one-time breakable preferential area of weakness 38. For example, in some embodiments, the breakable element 12 includes a resealable adhesive or cohesive seal. The one-time breakable preferential area of weakness 38 can be a score line, a series of perforations, a thinned area or a highly oriented region. Additionally, the preferential area of weakness 38 can be made in a manner to separate by cutting therethrough. The preferential area of weakness 38 inhibits tampering with the reclosable package 10 prior to being opened.

The reclosable package 10 can further include an optional slider mechanism 36 (FIG. 2) slidably mounted to the fastener 14 for movement between a closed position and an open position. Referring to FIGS. 1 and 2, the first and second profiles 26, 32 are engaged to each other while the slider mechanism 36 is in the closed position, and movement of the slider mechanism 36 from the closed position to the open position disengages the profiles 26, 32 from each other.

The package 10 of FIG. 2 also includes end terminations 37. End terminations can have various purposes such as (a) preventing or inhibiting the slider mechanism 36 from going past the ends of the fastener 14, (b) interacting with the slider 36 to give a tactile indication of being closed, (c) assisting in inhibiting or preventing leakage from the package 10, and (d) holding the first and second profiles 26, 32 together and providing additional strength in resisting stresses applied to the profiles 26, 32 during normal use of the package 10. Further details concerning the construction and operation of the slider mechanism 36 and the end terminations 37 can be obtained from U.S. Pat. No. 5,067,208 to Herrington, Jr. et al., the content of which is incorporated herein by reference in its entirety.

It is contemplated that other end terminations can be used instead of the above-described end terminations 37. For example, an end weld can be formed by heated bars pressed against the end of the fastener, ultrasonic welding, or other ways known in the art.

As illustrated in FIGS. 1 and 2, the reclosable package 10 of the present invention is opened by having a consumer grip the slider mechanism 36 and move it such that the first and second profiles 26, 32 of the respective first and second tracks 24, 30 are detached from each other. Next, the consumer tears open the breakable element 12 (if present) along the preferential area of weakness 38. Alternatively, the consumer may open the breakable element 12, if used, by cutting therethrough. The package can be resealed utilizing the fastener 14 and slider mechanism 36. Specifically, the consumer grips the slider mechanism 36 and moves it from the open position to the closed position so as to engage the complementary first and second profiles 26, 32.

A one-time breakable element 12 not only provides a consumer with the assurance that a newly purchased package has not been opened before, but also provides a good initial seal that preserves the freshness of the perishable contents of the package prior to its initial opening and can inhibit or prevent the active agent from being activated by an activation-triggering condition, such as moisture. Since the reclosable closure arrangements of FIG. 1 are located above the one-time breakable element, (i.e., the reclosable closure arrangement is further from the interior space), the operation of the reclosable closure arrangement is not hampered by the presence of the one-time breakable element.

As embodied in FIG. 1, an agent structure can be connected to the first body panel inner surface 16b or the body panel can be formed of the web material as described further, below. The active agent can include a substance known to provide a desired function or effect on a package or contents thereof. In some embodiments, the active agent includes an odor management agent, which functions to mask, neutralize, and/or reduce an undesirable odor. Further, the web material can include a color indicator and other active agents, as described above in more detail.

The agent structure 50 can be provided in a form and structure suitable for the desired effect of the agent and the structure of the package. For example, in some embodiments, the agent structure 50 can be in the form of a coating, a patch, a tape, a pouch, a combination thereof, or in any other form that can be carried by, or incorporated or integrated into the structure of the web material to form the package 10. Additionally or alternatively, the active agent can be printed onto an underlying layer of the web material, co-extruded therewith, sprayed, applied by dipping the web into the active agent, deposited by way of static attraction, cast, applied via electroless deposition, vapor deposition, fused or otherwise embedded into the web or through combinations of these methods. The selection of a mode for disposing the active agent on the web, such as in a coating, patch, pouch, or tape is often dependent on the type of active agent being used, and the desired indication. For example, an active agent in a powder form (e.g., minerals containing chemistry) can be placed in an air-permeable pouch, rather than a patch because it is often difficult to embed powders in a patch. Alternatively, an active agent in a powder form can be dusted onto and adhered to the web material, or mixed with the material of the web prior to extrusion. Non-limiting examples of powdery active agents that can be incorporated into the agent structure 50 include perlite, calcium carbonate, kaolin, and ASEPTROL™ antimicrobial manufactured by Engelhard.

If a tape or patch is used to support the agent structure 50, the tape or patch can be formed of a web of the invention and further include an adhesive, a patch-like component, and/or a release system such as a slip additive which assists in inhibiting or preventing the agent structure from sticking to the adhesive. For example, the release system can be located on a surface of the tape or patch that is located distally from the surface that contacts the body panel to which the tape or patch is to be attached, so that sticking is inhibited or prevented when the package is wound into a roll. Materials such as siloxane and glycerol monostearate can be among the components of such a release system.

In accordance with another aspect of the present invention, the active agent can be extruded with the web material that ultimately forms the body panel 16. For example, the active agent can be blended into the web material, e.g., in the form of a masterbatch and coextruded with the web, and thus the body panel, in oil or powder form, or can be distributed in the form of microcapsules in the material of the body panel 16.

In a particular embodiment, the active agent is microencapsulated prior to being integrated into the web material or package structure. Microencapsulation encloses the active agent within a polymeric material that can withstand heat during package processing and manufacturing, but which degrades, dissolves, or otherwise breaks open and releases the active agent upon contact with pre-determined environmental factors such as moisture. The active agent can be encapsulated into microcapsules, and the microcapsules can be interspersed with the molten material of the web material and extruded into the web material during bulk production.

The web material of body panel 16 can be otherwise impregnated with the active agent It is also contemplated that the active agent can be sprayed, brushed, coated, laminated, stamped, or otherwise applied onto the web material, and thus onto the body panel 16.

In some embodiments, the active agent includes one or more odor management agents. Advantageously, the odor management agent can be incorporated into the web materials to form packages configured for collecting garbage or waste to mask, neutralize, and/or reduce undesirable odors. An odor management agent can thus be incorporated into thermoplastic bags or liners and other containers, such as garbage or waste bags, diaper containers, laundry bags, storage bags, and disposable medical bags or containers.

In one embodiment, the odor management agent preferably includes a counteractant agent, a neutralizing agent and optionally a masking agent. The odor management agent is formulated such that, when the odor management agent is incorporated into the bags or liners and other containers of the invention, the bag or liners and other containers are substantially free of fragrance so as to have no detectable scent.

As used herein, the term "counteractant" agent refers to a low-odor, volatile compound or composition that reacts quickly with the human olfactory system. The volatility of a counteractant agent should be higher than that of the malodor molecule. Examples of a counteractant agent include derivatives of cyclohexyl alcohol and ester, including, 1-cyclohexyl-1-ethyl formate, 1-cyclohexyl-1-ethyl acetate, 1-cyclohexyl-1-ethyl proprionate, 1-cyclohexyl-1-ethyl isobutyrate, 1-cyclohexyl-1-ethyl n-butyrate, 1-cyclohexyl-1-propyl acetate, 1-cyclohexyl-1-propyl n-butyrate, 1-cyclohexyl-2-methyl-1-propyl acetate, 2-cyclohexyl-2-propyl acetate, 2-cyclohexyl-2-propyl propionate, 2-cyclohexyl-2-propyl isobutyrate, and 2-cyclohexyl-2-propyl n-butyrate, which are sold under the trade name Veilex™ and disclosed in U.S. Pat. No. 4,622,221, the contents of which is expressly incorporated by reference herein in its entirety. Counteractant agents further can include substituted monocyclic compounds, including 1-cyclohexylethan-1-yl acetate; 1-cyclohexylethan-1-yl butyrate; 1-cyclohexylethan-1-ol; 1-(4'-methylethyl)cyclohexylethan-1-yl propionate, and 2'-hydroxyl-1'-ethyl(2-phenoxy)acetate, which are sold under the trade name Veilex™ and disclosed in U.S. Patent Application Publication No. 20050106192, the contents of which is expressly incorporated by reference herein in its entirety. Other examples of counteractant agents include 4-cyclohexyl-4-methyl-2-pentanone, as disclosed in U.S. Pat. No. 4,009,253, and 4-ethylcyclohexyl methyl ketone and 4-isopropylcyclohexyl methyl ketone, as disclosed in U.S. Pat. No. 4,187,251, and those disclosed in U.S. Pat. Nos. 6,432,981, 6,610,648, 5,861,371, 5,441,727, 4,719,105 and 4,187,251, the contents of each which are expressly incorporated by reference herein in their entireties.

As used herein, the term "agent" refers to a compound, composition or formulation. A neutralizing agent can have a low level of scent associated therewith, or have no perceptible scent; however, when a neutralizing agent is used in combination with a counteractant agent to formulate an odor management agent, the bags or liners and containers having the amount of odor management agent incorporated in the bag therein are substantially free of fragrance so as to have no perceptible scent. It should be understood that the term "agent" and the term "odor management agent" do not necessarily connote a single chemical compound, but includes mixtures, formulations, combinations, compounds and compositions of components that need not interact to form a single chemical structure.

A neutralizing agent can have increased activity toward malodor molecules in the presence of humidity or moisture, such as for instance, when the neutralizing agent comes in contact with an aqueous solution having a malodor. Exemplary neutralizing agents include substituted esters such as lauryl methacrylate, sold under the trade name Metazene™ and disclosed in, for example, U.S. Pat. Nos. 2,554,093, 4,009,254, 4,257,176 as well as others, biguanides and quaternary ammonium compounds, such as those disclosed in U.S. Pat. No. 4,818,524; and esters of unsaturated monocarboxylic acids, such as those disclosed in U.S. Pat. No. 3,074,981, the contents of each of which are expressly incorporated by reference herein in their entireties.

U.S. Pat. Nos. 5,593,670, 5,668,097, 5,714,137, 5,783,544, 5,939,060 and 5,942,217, the contents of which are expressly incorporated by reference herein in their entireties, further disclose neutralizing agents that are uncomplexed cyclodextrins. U.S. Pat. No. 6,528,047, the contents of which is expressly incorporated by reference herein in its entirety, discloses neutralizing agents of a mixture of zinc ricinoleate compound and alkoxylated amine having the formula $R(nAO)_sNH_t$, wherein R is a saturated or unsaturated, linear or branched alkyl containing from 8 to 22 carbon atoms, AO is a $C_2$-$C_6$ alkoxylate, n is the number of moles of AO and is from 1 to 50, s is 1, 2 or 3, t is 0, 1 or 2, and the sum of s and t is 3. Additionally U.S. Pat. No. 4,968,496 discloses deodorant compositions using zinc ricinoleate compound as a malodor-binding compound, and U.S. Pat. No. 6,528,047 disclose home care odor formulations using a zinc ricinoleate compound as an odor-binding compound, the contents of which are expressly incorporated by reference herein in their entireties.

Examples of preferred neutralizing molecules include zinc ricinoleate compounds as sold under the trade name TegoSorb™ (Goldschmidt Chemical Corp., Hopewell, Va.), such as TegoSorb 50™, and as disclosed in U.S. Pat. No. 6,592,813, the content of which is expressly incorporated by reference herein in its entirety. Other compounds or compositions may be added to a zinc ricinoleate to provide additional malodor binding effect.

Generally, the counteractant agent and neutralizing agent, if used, have no perceptible scent. If desired, a masking agent also can be provided, however in an effective amount so that, when the odor management agent is incorporated into the bags or liners and containers, the bags or liners and containers are substantially free of fragrance so as to have no perceptible scent.

As used herein, the term "masking agent" refers to a perfume or fragrant compound that imparts a scent to mask the malodor. Common fragrances are within this category and include. The fragrance can be single or multiple components, and natural or artificial, and solid or liquid. In the present invention, the level of masking agent in the odor management agent should be so low as to impart no perceptible scent to a user.

The odor management agent can be formulated as a "masterbatch", which, as the term is used herein, refers to a concentrate of active agents, e.g., an odor management agent, dispersed in a carrier polymer, which carrier polymer is then blended with a matrix polymer to achieve a desired concentration of active agent in the product. For example, the odor management agent, which can be in an oil-based carrier, is added to a compounding extruder and compounded with the carrier polymer to create a masterbatch carrier polymer. The masterbatch carrier polymer is then blended with the matrix polymer and extruded into the web to form the panels of the bag.

The masterbatch can be formulated to include varying levels of odor management agents. By example and not limitation, the odor management agent, in the oil-based carrier, can be added from 10% to 25% by weight to the carrier polymer to produce the masterbatch. The masterbatch can then be added to and coextruded with the matrix polymer at from 1% to 4% (wt), to form the web having the odor management agent distributed therethrough. At a target input level of 2% (wt) masterbatch in the matrix polymer resin, the level of counteractant agent, such as a Veilex™ compound, in the web is approximately 0.5% by weight or 5,000 ppm, and the level of neutralizing agent, such as a zinc ricinoleate compound, in the web is approximately 0.625% by weight or 625 ppm. The level of counteractant agent in the web may preferably be from about 0.05% to 5.0% (wt) or 500 ppm to 50,000 ppm, and the level of neutralizing agent may be from about 0.005% to 0.5% (wt) or 50 ppm to 5,000 ppm.

Further in accordance with the invention, the web material or package can be provided with an activation system that is triggered automatically, such as when the reclosable package is opened or filled with contents. The activation system can be mechanical in nature, such as a perforation or a peel apart system that once separated initiates the release of the active agent. Another activation method can be based on the humidity or moisture level that is present in the package (e.g., which correlates to water activity of the contents). For example, a high amount of humidity can initiate a chemical or other reaction that subsequently releases a volatile chemical such as carbon dioxide or chlorine dioxide. In such an example, a greater amount of active agent is added when the humidity is higher in the reclosable package. Examples of reactions that are activated by a high humidity level are salt and acid reactions, such as sodium bicarbonate and citric acid, or sodium hypochlorite and citric acid.

During a method of operation of a reclosable package formed with the subject web materials having, for example, a humidity-activated odor management agent, perishables are placed in the interior of the package, and an increased humidity or moisture level in the perishables activates the odor management agent. Preferably, the reclosable package is formed of a barrier material as described to inhibit activation of the active agent due to the surrounding environment. Additionally, if the agent structure is disposed proximate the mouth of a bag-like package or proximate the rim of a container-like package, selective activation or release can be accomplished. For example, the humidity or moisture level of the perishables can activate the agent as the perishables travel in the vicinity of the agent (e.g., through the mouth or past the rim of the package during the initial placement of the perishable products into the interior), while the perishable products remain disposed in the interior, and upon entry of air into the interior (e.g., during an opening of the package). Disposing the agent structure proximate the mouth or rim of a package can also be advantageous when maximum display of the contents is desired in a transparent package.

A humidity activation method can further be controlled by providing a barrier layer material. For example, it is preferable that the web materials provide a barrier layer or be formed of a barrier material so as to create an enclosed environment to prevent or inhibit the introduction of humidity and the release of active agent when a package formed from the web material is closed. As used herein, the terms "barrier layer" and "barrier material" include layers or materials that inhibit or otherwise control the release of an active agent into a package atmosphere, rather than being limited to layers or materials that completely block or prevent such release.

An example of a barrier material is polyethylene glycol (PEG) incorporated into low density polyethylenes (LDPE). Other materials providing a barrier to transfer of water, water vapor, oxygen, nitrogen, carbon dioxide, ethylene, volatile or non-volatile active agents include but are not limited to polymers, copolymers, blends, extrusions, co-extrusions, coatings, metallization or laminations of: low density polyethylene (LDPE), linear low density polyethylene (LLDPE), linear medium-density polyethylene (LMDPE), high density polyethylene (HDPE), very low density polyethylene (VLDPE), metallocene (mPE), polypropylene (PP), oriented polypropylene (OPP), acrylonitrile butadiene styrene (ABS), acrylonitrile-styrene-acrylate (ASA), acrylonitrile-EPDM-styrene (AES), ASA/AES copolymers, polyamide 6, polyamide 66 and their copolyamides, poly vinyl chloride (PVC), acrylic, polybutylene terephthalate (PBT), ethylene/ethyl acrylate (EEA), ethylene/vinyl acetate (EVA), modified polystyrene, ethylene-vinyl alcohol (EVAL or EVOH), polyvinylidene chloride (PVDC), liquid crystal polymer (LCP), polyamides, polyacrylic acid (PAA), polylactic acid (PLA), polyethylene terephthalate (PET), polyethylene terephthalate glycol (PETG), saran, ceramic filled polymers, nanocomposite polymers, polychlorotrifluoroethylene (PCTFE), polymethyl methacrylate (PMMA), acrylonitrile-methyl acrylate (AC-MA), polyphenylene ether (PPE), polyphenylene oxide (PPO), thermoplastic elastomer, cellophane, nylon, modified polyolefins with barrier properties, cyclic olefin copolymers, polyacrylonitriles, acrylonitrile copolymers, polyacetals, modified polyesters, acrylic derivatives, and inorganic barrier coatings.

Preferred barrier materials include metal foil, polyethylene terephthalate (PET), metallized polymers, such as metallized polyester, polyvinylidene chloride (PVDC), and ethylene vinyl alcohol (EVOH).

Preferred materials that are suitable for blocking the introduction of water vapor into a package include low density polyethylene (LDPE), linear low density polyethylene (LLDPE), linear medium-density polyethylene (LMDPE), high density polyethylene (HDPE), polypropylene (PP), oriented polypropylene (OPP), acrylonitrile-methyl-acrylate (AMA), poly vinyl chloride (PVC), PMMA, acrylic, ethylene/vinyl acetate (EVA), polyvinylidene chloride (PVDC), polyethylene terephthalate (PET), polyethylene terephthalate glycol (PETG), saran, ceramic filled polymers, nanocomposite polymers, polychlorotrifluoroethylene (PCTFE), polymethyl methacrylate (PMMA), acrylonitrile-methyl acrylate (AC-MA), modified polyolefins with barrier properties, cyclic olefin copolymers, polyacrylonitriles, acrylic derivatives, inorganic barrier coatings, foils and metallized polymers, polyvinylfluoride (PVF), ionomer, polyetherimide, Polyethylene naphthalate (PEN), Butyl rubber, and polychloroprene (Neoprene G).

Preferred materials that are suitable for blocking the release of active agents and/or oxygen from a package include high density polyethylene (HDPE), polypropylene (PP), oriented polypropylene (OPP), acrylonitrile-methyl-acrylate (AMA), poly vinyl chloride (PVC), PMMA, acrylic, polyvinylidene chloride (PVDC), polyethylene terephthalate (PET), polyethylene terephthalate glycol (PETG), saran, ceramic filled polymers, nanocomposite polymers, polychlorotrifluoroethylene (PCTFE), polymethyl methacrylate (PMMA), acrylonitrile-methyl acrylate (AC-MA), modified polyolefins with barrier properties, cyclic olefin copolymers, polyacrylonitriles, acrylic derivatives, inorganic barrier coatings, foils and metallized polymers, Polyvinylfluoride (PVF), Polyetherimide, Polyethylene naphthalate (PEN), Polyvinylidene fluoride (PVDF), polyimide, polyetheretherketone (PEEK), polyoxymethylene (POMC), polyacetal, acrylonitrile butadiene styrene (ABS), polyamide 6, polyamide 66 and their copolyamides, polybutylene terephthalate (PBT), thermoplastic polyester (TPE), modified polystyrene, ethylene-vinyl alcohol (EVAL or EVOH), polyamides, polylactic acid (PLA), cellophane, nylon, modified polyesters, and polyethersulfone (PES).

Of the foregoing materials, those that are suitable as barrier layers for blocking both the introduction of water vapor to and the release of active agents from a package include high density polyethylene (HDPE), polypropylene (PP), oriented polypropylene (OPP), acrylonitrile-methyl-acrylate (AMA), poly vinyl chloride (PVC), PMMA, acrylic, polyvinylidene chloride (PVDC), polyethylene terephthalate (PET), polyethylene terephthalate glycol (PETG), saran, ceramic filled polymers, nanocomposite polymers, polychlorotrifluoroethylene (PCTFE), polymethyl methacrylate (PMMA), acrylonitrile-methyl acrylate (AC-MA), modified polyolefins with barrier properties, cyclic olefin copolymers, polyacrylonitriles, acrylic derivatives, inorganic barrier coatings, foils and metallized polymers, Polyvinylfluoride (PVF), Polyetherimide, and Polyethylene naphthalate (PEN).

It is also contemplated that other barrier materials such as foils and metallized polymers such as metallized oriented polypropylenes (OPP) can be used. The barrier layer is substantially impermeable to at least water vapor and active agents, and, in some embodiments, also to oxygen, nitrogen, and carbon dioxide, or combinations thereof. The barrier layer thus inhibits or prevents water vapor (and, in some embodiments, oxygen, nitrogen, and carbon dioxide) from entering the interior of the package, while inhibiting or preventing the active agent from escaping the interior of the package. An example of a cyclic olefin copolymer that can be used in forming the barrier layer is TOPAS™ 8007. Useful cyclic olefin copolymers are believed to be available from several companies. For example, Ticona, a business of Celanese AG, in Summit N.J. has cyclic olefin copolymers available. Other companies that are believed to have cyclic olefin copolymers available include Nippon Zeon (Japan), Mitsui Chemical (Japan) and JSR (Japan), formerly know as Japan Synthetic Rubber. Ticona, a business of Celanese AG, has commercially available cyclic olefin copolymers (COCs) under the designation TOPAS™. These cyclic olefin copolymers are believed to be prepared with feedstocks of norbornene and ethylene and the use of a metallocene catalyst. There are believed to be at least four grades of TOPAS™ resins available (TOPAS™ 8007, TOPAS™ 6013, TOPAS™6015 and TOPAS™ 6017). The four grades of TOPAS™ resins available have glass transition temperatures, $T_g$, of 80, 140, 160 and 180° C., respectively. The corresponding norbornene levels of the four grades of TOPAS™ resins are 35, 48, 55 and 59 mole %.

Preferably, the web material includes thermoplastic materials. For example, a polymeric matrix layer can be provided for impregnating or supporting a microencapsulated active agent therein. The matrix layer of the agent structure 50 can be made of polyolefinic materials such as polyethylenes, polypropylenes, polystyrenes, and combinations thereof. Non-limiting examples of the matrix layer materials include polymers, copolymers or blends of: low density polyethylene (LDPE), linear low density polyethylene (LLDPE), linear medium-density polyethylene (LMDPE), high density polyethylene (HDPE), very low density polyethylene (VLDPE), metallocene (mPE), polypropylene (PP), polyamide 6 polyamide 66 and their copolyamide, poly vinyl chloride (PVC), acrylic, thermoplastic polyester (TPE), ethylene/vinyl acetate (EVA), polystyrene (PS), high impact polystyrene (HIPS), modified polystyrene, liquid crystal polymer (LCP), polyamides, polyacrylic acid (PAA), polylactic acid (PLA), polyethylene terephthalate glycol (PETG), polymethyl methacrylate (PMMA), polyphenylene ether (PPE), thermoplastic elastomer, and cellulose and filled plastics. These materials generally provide a good barrier to water vapor, but allow permeation of oxygen and active agents. Polyethylene is particularly advantageous because of its recyclability. Another example of a material that can be used to form the web material is ethyl methyl acrylate (EMA). A surface of web material can be formed of a porous non-woven material (e.g., gauze) that allows the active agent such as odor management agent or other active agent to be released. For odor management, one of the layers of the odor management structure can further include a fragrance (e.g., a liquid fragrance), a scent-enhancing mineral, and/or a polymeric resin (e.g., LLDPE).

As will be understood by those of ordinary skill in the art, the amount of agent to be used in combination with a package will depend on the environment in which the agent is in use, e.g., the loss and release rates of the agent. The release rate refers to the rate at which the agent is released into the interior of the package, and the loss rate refers to the rate at which the released agent escapes from the interior of the package. Preferably, the agents of the present invention are disposed in amounts such that the release rate of the agent is greater than the loss rate of the agent during a pre-determined "shelf life" or duration of use, so that the presence of agent in the interior of a package is replenished faster than it is lost, thus ensuring effective performance of the agent. The loss rate of the agent depends upon a variety of factors related to package design, construction, and use.

It is contemplated that additional layers can be used as part of the package to enhance performance of the active agent. For example, a barrier layer can assist in keeping the active agent, e.g., odor management agent, in communication with the interior of the reclosable package and, thus, assist in preventing or inhibiting the odor management agent from permeating through the body panel. Similarly, the barrier layer, when used to define the package, inhibits humidity or other activators from activating the active agent.

For example, and with reference to the package embodiment of FIG. 1, each of the opposing body panels 16, 18, preferably forms a barrier layer that is substantially impermeable to at least water vapor and active agents and, in some embodiments, also to oxygen, nitrogen, carbon dioxide, or combinations thereof. The opposing body panels 16, 18 thus can include, i.e., be at least partially formed from one or more of, the foregoing materials. The opposing body panels 16, 18 can include barrier layers located on exterior and/or interior surfaces of the packages.

Based upon the above, the web material of the invention, which includes a barrier layer with active agent carried thereon, can be used to form a portion of a package, such as a body panel, a lidding material or a wrap. Alternatively, the web material of the invention can be formed to define an agent structure for use with a package or as otherwise desired.

For purposes of illustration, disclosed packages of the present invention will now be further described herein with respect to odor management agents incorporated in or carried by agent structures of the invention. Those of ordinary skill in the art will understand that the disclosed packages can be suitably modified to include other types of active agents.

Figure 3A:
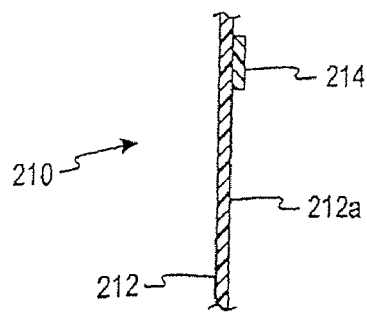
FIG. 3a is a partial cross-sectional view of one side of a reclosable package or bag comprising a polymeric structure with one layer according to one embodiment of the present invention.

In one such embodiment, the barrier layer can define or otherwise be located on an inner surface of an odor management structure as shown in, for example, FIG. 3a. In FIG. 3a, one side of a package 210 is depicted with a body panel 212 that includes an odor management structure 214, and a second body panel (not shown in FIG. 3a). The odor management agent of the odor management structure 214 is in communication with the interior space, while one surface of the odor management structure 214 is attached to a surface 212a of the body panel 212 via an adhesive, a heat seal, or a weld, e.g., an ultrasonic weld. It is contemplated that other attachment methods can be used. For example, the odor management structure can be attached to at least one surface of the body panels, using mechanical methods such as clips or staples.

Further, the odor management structure can be provided as a coextrusion structure or as a laminate. Alternatively, it can be coated on a layer of film. In accordance with the invention, the web material thus includes the body panel 212 of the embodiment of FIG. 3a with the active agent disposed thereon.

Alternatively, and as previously noted, the web material can be formed into a separate agent structure, having a base layer with the active agent carried by the base layer. The base layer can be made of a barrier layer, or a diffusion material with the active agent contained therein, and/or can have the active agent disposed between the base layer and removable covers. Alternatively or additionally, a diffusion layer can be disposed between the base layer and the removable covers and/or a barrier layer can be provided on the base layer opposite the removable covers. The barrier layer, base layer and diffusion layers are, in one embodiment, preferably are made of polypropylene, polyethylene, and ethylmethyl acrylate, respectively.

The separate agent structure can be in the form of a patch, a tape or a pouch. By providing an adhesive, the agent structures can be adhered to a body panel of the package. If attached to the web material, that is, ultimately attached a wall or body panel of a package, such attachment can be facilitated by an adhesive, cohesive, fusion or weld connection. In alternate embodiments, the agent structures can simply be placed within the package.

Figure 3B:
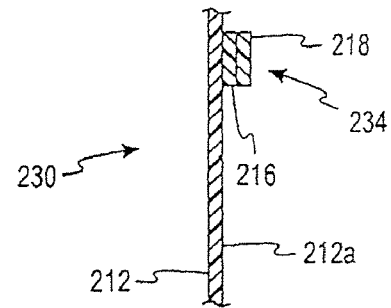
FIG. 3b is a partial cross-sectional view of one side of a reclosable package or bag comprising a polymeric structure with two layers according to one embodiment of the present invention.

One example depicted in FIG. 3b includes a reclosable package 230 comprising a first body panel 212, a second body panel (not shown in FIG. 3b), and an odor management structure 234. The structure 234 comprises a first layer 216 that is a barrier layer and a second polymeric layer 218 that includes an odor management agent. The first layer 216 can be a polymeric barrier layer using one of the previously mentioned barrier materials. One example of a polymer that can be used in the second polymeric layer 218 is a polyolefin such as a linear low density polyethylene (LLDPE). An outer surface 216a of the first layer 216 of FIG. 3b is attached to an inner surface 212a of the first body panel 212. The second polymeric layer 218 is directly adjacent to the first layer 216 so that the odor management agent is in communication with the interior space. Depending on the materials that form the first and second layers 216, 218, it may not be necessary to adhesively attach the layers together. Rather, for example, the first and second layers can be co-extruded together if the materials for forming the first and second layers are compatible. In the embodiment of FIG. 3b, the body panel 212 need not be a barrier material, since a layer 216, providing barrier function is already provided, although it is preferred that the body panel 212 include barrier characteristics.

It is also contemplated that information can be printed on the odor management structure 234 such as on the barrier layer. It is contemplated that the printing can occur on different locations of the structure. For enhanced visibility and readability of the printing, it may be desirable to print on the surface of the odor management structure that is closest to the body panel when the structure is located in the interior of the reclosable package. For example, in FIG. 3b, the printing would be desirably located between the first body panel 212 and the first layer 216. If adhesive is used to attach the first layer 216 of FIG. 3b to the surface 212a, then the printing can be located between the adhesive and the first layer 216. It is contemplated that other attachment methods can be used such as a heat seal or mechanical methods.

Figure 3C:
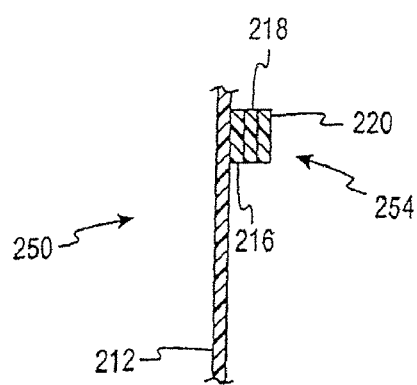
FIG. 3c is a partial cross-sectional view of one side of a reclosable package or bag comprising a polymeric structure with three layers according to one embodiment of the present invention.

Referring to FIG. 3c, a reclosable package 250 comprises a first body panel 212, a second body panel (not shown in FIG. 3c), and an odor management agent structure 254 in the form of a patch or tape. It is contemplated that the structure can be in the form of a pouch or a coating. The odor management agent structure 254 comprises a first layer 216 that is a barrier layer, and a second polymeric layer 218 that includes an odor management agent, and a third polymeric layer 220 that is a diffusion layer. The first layer 216, as discussed above, can be a polymeric layer. The second polymeric layer 218 that includes the odor management agent is located between the first and third layers 216, 220. One example of a polymer that can be used in the second polymeric layer 218 is a polyolefin, such as a linear low density polyethylene (LLDPE). The odor management agent is in communication with the interior space of the reclosable package via the third polymeric layer 220 that is permeable. Thus, the third polymeric layer 220 controls the permeability and must be permeable to the extent that the odor management agent can enter the interior of the reclosable package therethrough.

It is contemplated that the third polymeric layer 220 can comprise a cyclic olefin copolymer. The third polymer layer can comprise from about 10 to about 80 (wt) % or, more specifically, from about 20 to about 40 (wt) % cyclic olefin copolymer to assist in reducing curling of the polymeric structure. While not being bound by theory, curling tends to be caused when the materials forming the polymeric-structure layers are not as compatible with each other because of, for example, their different shrink rates. The barrier layer can comprise a more crystalline material that does not shrink much, if any, over time as compared to the diffusion layer that can comprise a material, such as polyethylene, that tends to shrink over time. The disadvantage of such structure curl is that the edges tend to curl in a transverse direction upon itself and therefore cause processing problems. The curling of the polymeric structure can be reduced or inhibited by using a cyclic olefin copolymer in the third polymeric layer, whereby the first layer and the third polymeric layer become more compatible. The addition of a cyclic olefin copolymer to the third polymeric layer 220 also slows the permeation of the odor management agent into the interior of the reclosable package 250.

As discussed above, it is contemplated that the odor management structure 254 of FIG. 3c can have a release agent (e.g., a slip additive) that assists in preventing or inhibiting the polymeric structure from sticking to itself. It is also contemplated that information can be printed on the structure 254. The first layer 216 can be attached to the surface of the body panel(s), via an adhesive, heat seal or other methods.

Figure 3D:
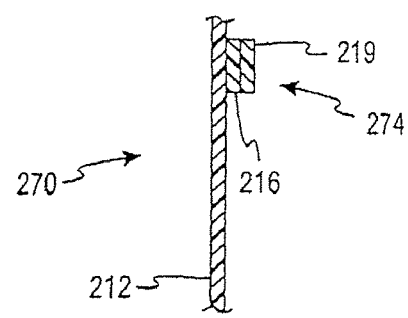
FIG. 3d is a partial cross-sectional view of one side of a reclosable package or bag comprising a polymeric structure with two layers according to another embodiment of the present invention.

Referring to FIG. 3d, a reclosable package 270 comprises a first body panel 212, a second body panel (not shown in FIG. 3d), and an odor management structure 274 in the form of a patch or tape. It is contemplated that the structure 274 can be a pouch. The odor management structure 274 comprises a first layer 216 being a barrier layer, and a second polymeric layer 219 being a diffusion layer and including an odor management agent. The odor management agent must be able to communicate with the interior space of the reclosable package or bag. The first layer 216 can be attached to the body panel 212, via an adhesive, a heat seal, a weld, or other methods.

The reclosable package can include more than one odor management or "agent" structure that includes an odor management agent therein.

An odor management structure (e.g., an odor management agent containing patch, tape, pouch, or coating) can vary in size and is dependent on factors such as the desired amount of odor management, the particular odor management agent being used, the number of odor management structures being used in a package, and the size of the package. The dimensions of the odor management structure are generally from about ½ inch or 1 inch to about 12 inches. Non-limiting examples of odor management structure dimensions include ½ inch×1 inch, 1 inch by 1 inch, ½ inch×2 inches, 1 inch×6 inches, 2×4 inches, and 4×12 inches. The thicknesses of the odor management structures can vary in the present invention but are generally less than about 20 mils. In some embodiments, the thickness of the structures is preferably about 12 to 16 mils, and more preferably about 14 to 15 mils. In other embodiments, the thickness of the structures is preferably about 5 to 10 mil, and more preferably 5 to 6 mil.

According to another embodiment, the odor management structure can include a non-woven matrix. The non-woven matrix can be impregnated after the non-woven matrix has been formed. The impregnation of the non-woven matrix can be accomplished by an odor management agent coating. Alternatively, the non-woven matrix can be initially formed with the odor management agent therein. According to a further embodiment, the odor management agent of the agent structure can be micro-encapsulated in an odor management structure.

The odor management structure being a patch, tape, pouch, or coating in one embodiment is located in, or in communication with the interior of a package or bag, such as the reclosable package 10. For example in FIG. 3a, a partial cross-sectional view of one side of the reclosable package 210 is depicted with the body panel 212 and the odor management n structure 214. The structure 214 is attached to an interior surface 212a of the body panel 212 in which the interior surface 212a forms an interior portion of the reclosable package 210.

Figure 4:
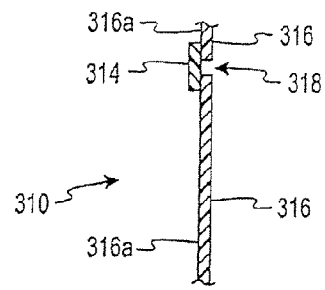
FIG. 4 is a partial cross-sectional view of one side of a reclosable package or bag according to another embodiment of the present invention.

Alternatively, the odor management structure being a coating, patch, pouch, or tape can be located on an exterior surface of an article or within layers of an article such that the odor management agent is able to permeate into or communicate with the interior of the reclosable package. For example, the odor management structure being a coating, patch, pouch, or tape can be located on the web material so as to be on an exterior surface of a reclosable package in which a portion of the body panel is removed such that the odor management agent from the odor management structure can permeate into the interior of the reclosable package. For example, referring to FIG. 4, a partial cross-sectional view of a web material for forming at least one side of a reclosable package 310 is shown with an odor management structure 314 attached to an exterior surface 316a of a body panel 316. The body panel 316 has at least one opening 318 that allows the odor management agent from the odor management structure 314 to permeate into the interior of the reclosable package 310. The opening(s) 318 can be one large opening or a plurality of smaller openings that extends from and through the body panel 316 of the reclosable package 310. The opening(s) 318 can be formed by processes known in the art including a perforation process.

Figure 5:
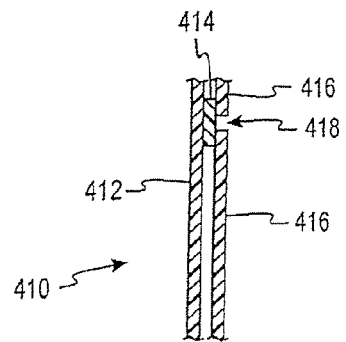
FIG. 5 is a partial cross-sectional view of one side of a reclosable package or bag according to a further embodiment of the present invention.

In another example, FIG. 5 depicts a partial cross-sectional view of a web material for forming at least one side of a reclosable package or bag 410. The reclosable package or bag 410 comprises an exterior layer 412, an odor management structure 414, and an interior layer 416 with opening(s) 418. The odor management structure 414 is located between and attached to the exterior layer 412 and the interior layer 416. The opening(s) 418 allows the odor management agent from the structure 414 to be in communication with the interior of the reclosable package or bag 410. The odor management structure can be inserted between the interior layer 416 and exterior layer 412 during manufacture of the web material, prior to forming the web material into the reclosable package or bag 410.

Figure 6:
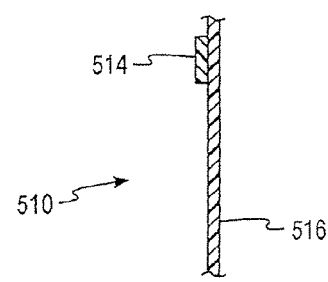
FIG. 6 is a partial cross-sectional view of one side of a reclosable package or bag according to yet another embodiment of the present invention.

It is contemplated that a layer of a reclosable package can be permeable to the odor management agent of the odor management structure such that the odor management agent is in communication with the interior of the reclosable package. FIG. 6 depicts such an example where a partial cross-sectional view of a web material for forming a reclosable package 510 is shown. The reclosable package 510 comprises an odor management structure 514 and a diffusion layer 516. The diffusion layer 516 allows the odor management agent from the odor management structure 514 to enter the interior of the reclosable package. The odor management structure 514 can be attached to the diffusion layer 516 during manufacture of the web material, prior to forming the web material into the reclosable package or bag 510.

The diffusion layer 516 can be made of a suitable material that allows the odor management agent to reach the interior of the reclosable package in a relatively quick fashion. Thus, materials providing permeation of water, water vapor, oxygen, nitrogen, carbon dioxide, ethylene, volatile actives or nonvolatile active agents can be used for the diffusion layer. Examples of a diffusion layer 516 include polymers, copolymers, blends, extrusions, co-extrusions, coatings or laminations of: low density polyethylene (LDPE), linear low density polyethylene (LLDPE), very low density polyethylene (VLDPE), metallocene (mPE), polypropylene (PP), acrylonitrile butadiene styrene (ABS), polyamide 6, polyamide 66 and their copolyamides, poly vinyl chloride (PVC), acrylic, polybutylene terephthalate (PBT), thermoplastic polyester (TPE), ethylene/ethyl acrylate (EEA), ethylene/vinyl acetate (EVA), polystyrene (PS), high impact polystyrene (HIPS), modified polystyrene, ethylene-vinyl alcohol (EVAL or EVOH), polyacrylic acid (PAA), polylactic acid (PLA), filled polymers, hydrophilic nanocomposite polymers, polymethyl methacrylate (PMMA), thermoplastic eastomers, polydimethylsiloxane (PDMS), polymethylpentene (PMP), polyvinyl acetate (PVA), polyvinyl alcohol (PVAL), and cellulose acetate (CA), all of which have general affinity for moisture.

As will be understood by those of ordinary skill in the art, the same type of polymer material can be used in forming either the matrix, barrier, or diffusion layer, depending on the percentage ratio of the material in the layer composition, the quantity of the material in the layer composition (e.g., the thickness of the layer composition), and/or the method of fabrication. Thus, the use of a particular polymer material as a component for the matrix, barrier, or diffusion layer depends on its amount and manner of use.

Figure 7:
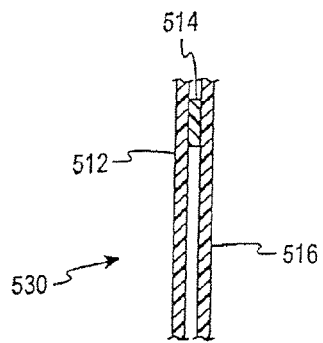
FIG. 7 is a partial cross-sectional view of one side of a reclosable package or bag according to yet a further embodiment of the present invention.

FIG. 7 depicts another embodiment with a partial cross-sectional view of a web material for forming at least one side of a reclosable package 530 that includes an additional layer (exterior layer 512) as compared to the reclosable package 510 of FIG. 6.

It is contemplated that additional layers can be added in forming the web materials and reclosable packages shown in FIGS. 3-7. For example, an ethylene vinyl alcohol (EVOH) copolymer or polyvinylidene chloride layer (PVDC) can be used in forming the body panels of the reclosable package, or in forming a barrier layer of the package. Such a barrier layer assists in keeping the odor management ingredient in communication with the interior of the reclosable package. Other layers are also contemplated. An odor management enhancing layer can operate to enhance delivery of the odor management agent with increasing humidity. Such an odor management enhancing layer is particularly advantageous, since increased humidity often results in a corresponding increase in bacterial growth that leads to increased perishable spoiling. One example of an odor management enhancing layer is polyvinyl alcohol (PVOH).

Figure 8:
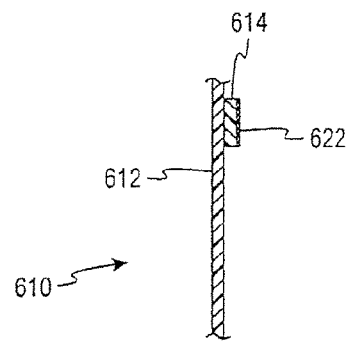
FIG. 8 is a partial cross-sectional view of one side of a reclosable package or bag according to another embodiment of the present invention.

The odor management structure can include one or more peelable covers. An example of such an embodiment is depicted in FIG. 8 where a partial cross-sectional view of a web material for forming one side of a reclosable package 610 comprises a body panel 612, an odor management structure 614, and a peelable cover 622. The peelable cover 622 covers at least a portion of the odor management structure 614 and may cover the entire odor management structure 614 that is exposed in the interior of the reclosable package 610. The peelable cover 622 prevents or inhibits the odor management agent from escaping the odor management structure 614 in its initial position shown in FIG. 8. The peelable cover can be attached to the body panel 612 and/or the odor management structure 614. The peelable cover 622 is removed by a user from the odor management structure 614 to enhance or begin the release of the odor management agent from the odor management structure 614. Typically, the removal of the peelable cover 622 by the user occurs when a package is going to have perishable placed into it. One example of the peelable cover 622 is a barrier layer such as EVOH or PVDC. It is contemplated that a peelable cover can be used with any of the odor management structures that are in the form of a patch, tape, or pouch.

According to another embodiment, a web material can be provided that yields a reclosable package having two odor management structures. For example, referring to FIG. 9a, a reclosable package 710 comprises a first thermoplastic body panel 712, a second thermoplastic body panel (not shown in FIG. 9a) a first odor management structure 714a, and a second odor management structure 714b. As discussed above, the first and second body panels are joined along a pair of opposing sides and a bottom bridging the sides so as to form an open mouth. The joined first and second body panels form an interior space for storing items.

Figure 9A:
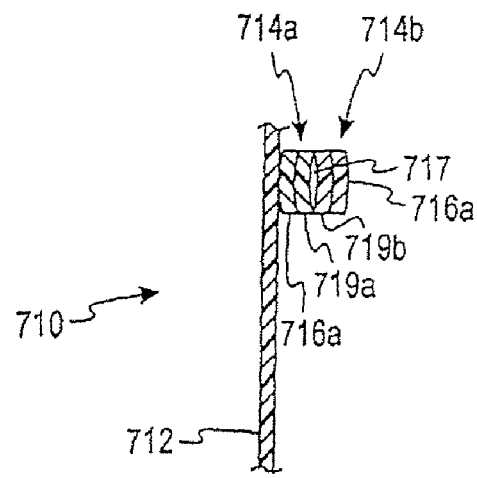
FIG. 9a is a partial cross-sectional view of one side of a reclosable package or bag that includes a polymeric structure with four layers according to one embodiment of the present invention.

The first odor management structure 714a comprises two layers and is a patch or tape. It is contemplated that the first and second odor management structures can form a pouch. The first odor management structure 714a comprises a first layer 716a being a barrier layer, and a second polymeric layer 719a being a diffusion layer and including an odor management agent. The first layer 716a can be a polymeric layer. The second polymeric layer 719a is directly adjacent to the first layer 716a. The first layer 716a is shown in FIG. 9a as being attached to the web material which forms the first body panel 712 via an adhesive, heat seal or other methods.

Similarly, the second odor management structure 714b comprises two layers and is a patch or tape. The second odor management structure 714b comprises a third layer 716b being a barrier layer, and a fourth polymeric layer 719b being a diffusion layer and including an odor management agent. The fourth polymeric layer 719b is directly adjacent to the third layer 716b. The third layer 716b can be a polymeric layer. The second polymeric layer 719a is releasably heat sealed at selected locations to the fourth polymeric layer 719b such that the respective odor management agent permeates into the interior of the reclosable package 710 via interior area 717.

The interior area 717 can be formed by having the first and second odor management structures 714a, b curl with respect to each other. As shown in FIG. 9a, the interior area 717 is formed between the second and fourth polymeric layers 719a, b. A slight curl of the odor management structures enables the odor management agent to be in communication with the interior of the reclosable package. It is desirable to have some curl in the embodiment depicted in FIG. 9a to assist in enabling the odor management agent to be in communication with the interior of the reclosable package or bag. As discussed above, the curling of the odor management structures can be formed from using materials for forming the odor management structures that are less compatible (i.e., the shrink rates of the materials differ).

It is contemplated that additional layers can be used in forming the two odor management structures. For example, in FIG. 9b, a reclosable package 730 comprises a first thermoplastic body panel 712, a second thermoplastic body panel (not shown in FIG. 9b), a first odor management structure 734a, and a second odor management structure 734b. The first and second body panels are joined along a pair of opposing sides and a bottom bridging the sides so as to form an open mouth. The joined first and second body panels form an interior space for storing items.

Figure 9B:
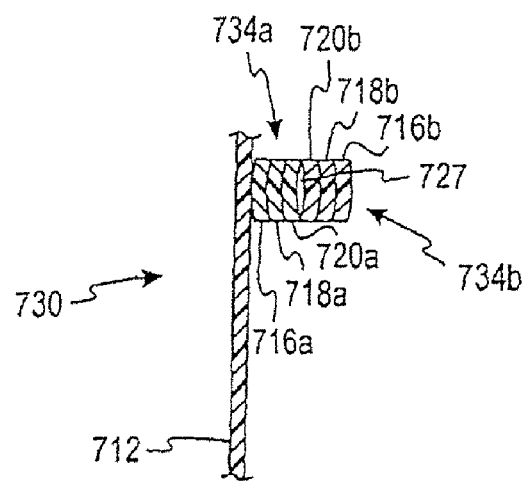
FIG. 9b is a partial cross-sectional view of one side of a reclosable package or bag that includes a polymeric structure with six layers according to one embodiment of the present invention.

The first odor management structure 734a comprises three layers and is a patch or tape. It is contemplated that the first and second odor management structures can form a pouch or a coating. The first odor management structure 734a comprises a first layer 716a being a barrier layer, a second polymeric layer 718a comprising an odor management agent, and a third polymeric 720a being a diffusion layer. The first layer 716a can be a polymeric layer. The second polymeric layer 718a is located between the first and third layers 716a, 720a. The first layer 716a is shown in FIG. 9b as being attached to the web material that forms the first body panel 712 via an adhesive or heat seal such that the odor management agent is in communication with the interior space. It is contemplated that other attaching methods can be used such as mechanical devices like clips or staples.

Similarly, the second odor management structure 734b comprises three layers and is a patch or tape. The second thermoplastic odor management structure 734b comprises a fourth layer 716b being a barrier layer, a fifth polymeric layer 718b comprising an odor management agent, and a sixth polymeric layer 720b being a diffusion layer. The fourth layer 716b can be a polymeric layer. The fifth polymeric layer 718b is located between the fourth and sixth polymeric layers 716b, 720b. The third polymeric layer 720a is heat sealed at selected locations to the sixth polymeric layer 720b such that the respective odor management agent of the second polymeric layer 718a and the fifth polymeric layer 718b is adapted to enter the interior space of the reclosable package between the third polymeric layer 720a and the sixth polymeric layer 720b.

As discussed above, an interior area 727 can be formed by having the first and second odor management structures 734a, 734b curl with respect to each other. As shown in FIG. 9b, the interior area 727 is formed between the third and sixth polymeric layers 720a, 720b.

Figure 10A:
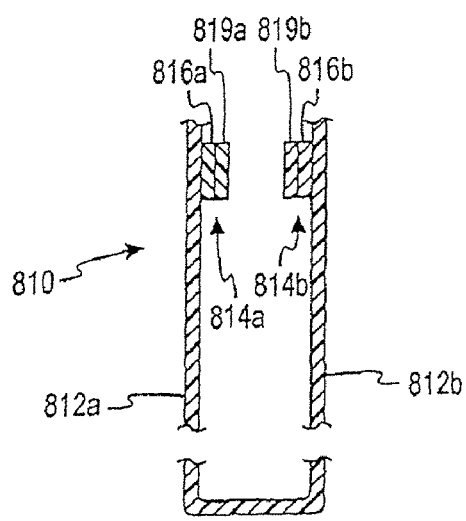
FIG. 10a is a partial cross-section view of two sides of a reclosable package or bag that includes two polymeric structures that each comprise two layers according to one embodiment of the present invention.

According to another embodiment, a reclosable package 810 is shown in FIG. 10a comprising a first thermoplastic body panel 812a, a second thermoplastic body panel 812b, a first odor management structure 814a, and a second odor management structure 814b. The first and second body panels 812a, 812b are joined along a pair of opposing sides and a bottom bridging the sides so as to form an open mouth. The joined first and second body panels form an interior space for storing items.

The first odor management structure 814a comprises two layers and is a patch or tape. It is contemplated that the first and second odor management structures can be in the form of a pouch. The first odor management structure 814a comprises a first layer 816a being a barrier layer, and a second polymeric layer 819a being a diffusion layer and including an odor management agent. The first layer 816a can be a polymeric layer. The second polymeric layer 819a is directly adjacent to the first layer 816a. The first layer 816a is shown in FIG. 10a as being attached to the web material, which forms the first body panel 812a via an adhesive or heat seal. It is contemplated that other attachment methods may be used. To adhere to the web material, which forms the first body panel 812a, the first layer 816a can include a coating that is not sticky or tacky at room temperature. Such a coating may become sticky, for example, at higher temperatures, or upon exposure to infrared radiation or heat.

Similarly, the second odor management structure 814b comprises two layers and is a patch or tape. The second odor management structure 814b comprises a third layer 816b being a barrier layer, and a fourth polymeric layer 819b being a diffusion layer and including an odor management agent. The third layer 816b can be a polymeric layer. The fourth polymeric layer 819b is directly adjacent to the third layer 816b. The third layer 816b is shown in FIG. 10a as being attached to the web material, which forms second body panel 812b via an adhesive or heat seal. It is contemplated that other attachment methods may be used. To adhere to the web material, which forms the second body panel 812b, the third layer 816b may include a coating that is not sticky or tacky at room temperature. Such a coating may become sticky, for example, at higher temperatures, or upon exposure to infrared radiation or heat.

It is contemplated that the first odor management structure and the second odor management structure can be formed of different compositions. For example, the first structure can include a first odor management agent, while the second structure may be a second odor management agent, and may include a color indicator, for example. In forming such an embodiment, the first and second odor management structures can, for example, be formed by extruding two different patches, tapes, pouches, or by applying two different coatings.

Figure 10B:
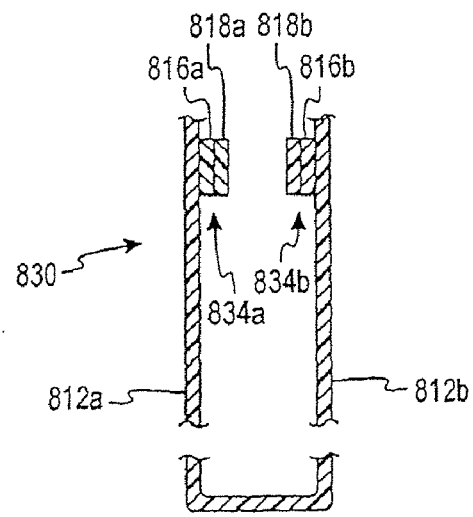
FIG. 10b is a partial cross-section view of two sides of a reclosable package or bag that includes two polymeric structures that each comprise two layers according to another embodiment of the present invention.

Alternatively, the reclosable package can be formed by other than two or more layer structures. For example, a barrier layer need not be provided if the web material used to form the body panels 812 are formed of a material suitable to function as a barrier layer. Furthermore, as shown in FIG. 10b, a reclosable package 830 includes a first odor management structure 834a that comprises a first layer 816a that comprises an odor management agent, and a second polymeric layer 818a that is a diffusion layer. The reclosable package 830 also includes a second odor management structure 834b that comprises a third layer 816b that comprises an odor management agent, and a fourth polymeric layer 818b that is a diffusion layer. It is contemplated that the first and second odor management structures can be made of different compositions, such as being made of different odor management agents or diffusion layers.

Figure 10C:
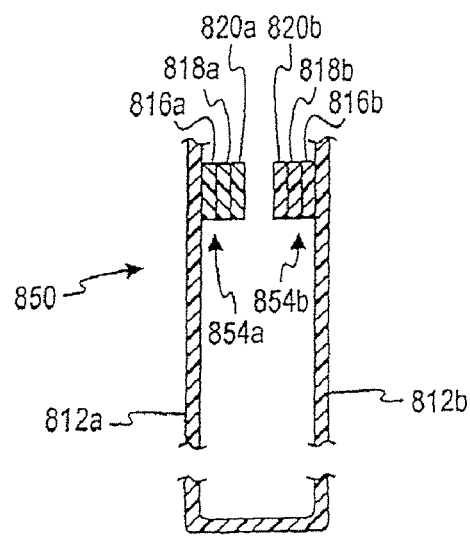
FIG. 10c is a partial cross-section view of two sides of a reclosable package or bag that includes two polymeric structures that each comprise three layers according to one embodiment of the present invention.

According to yet another embodiment, the reclosable package can be formed by three or more layers. For example, as shown in FIG. 10c, a reclosable package 850 made from a web material in accordance with the invention includes a first odor management structure 854a that comprises a first layer 816a that is a barrier layer, a second polymeric layer 818a that comprises an odor management agent, and a third polymeric layer 820a that is a diffusion layer. The reclosable package 850 includes a second odor management structure 854b that comprises a fourth layer 816b that is a barrier layer, a fifth polymeric layer 818b that comprises an odor management agent, and a sixth polymeric layer 820b that is a diffusion layer. The first and second odor management structures 854a, b are attached to first and second body panels 812a, 812b, respectively, via an adhesive or heat seal. It is contemplated that the first and second structures can be made of different compositions, such as being made of different barrier materials or odor management agents.

As previously described, the odor management agents of the present invention can contain an activation system that is triggered by a user opening a reclosable package or placing contents therein. In some embodiments, such as the embodiment shown and described with respect to FIG. 8, the activation system of the odor management agents of the present invention is mechanical in nature. For example, in the embodiment of FIG. 8, the activation system includes a perforation or a peel-apart system which, once separated, initiates the release of the odor management agent.

Figure 11A:
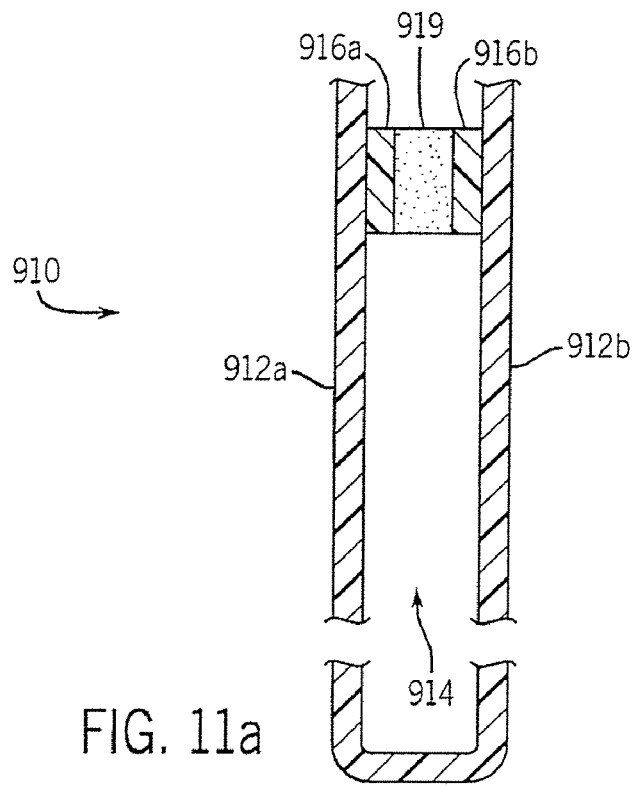
FIG. 11a is a partial cross-section view of two sides of a reclosable package or bag with a polymeric structure disposed therebetween, in which the polymeric structure includes a one-time breakable element.

In accordance with another such aspect of the invention, a reclosable package 910, made from a web material in accordance with the invention, is shown in FIG. 11*a*, including a first thermoplastic body panel 912*a*, a second thermoplastic body panel 912*b*, and an odor management structure 914 disposed therebetween. The first and second body panels 912*a*, 912*b* are joined along a pair of opposing sides and a bottom bridging the sides so as to form an open mouth. The joined first and second body panels form an interior space for storing items. The odor management structure 914 can be in the form of a patch or tape as embodied herein, and comprises three layers. Particularly, the odor management structure 914 depicted in FIG. 11*a* comprises a first layer 916*a* being a barrier layer, a second polymeric layer 919 being a frangible diffusion layer with an odor management agent, and a third layer 916*b* being a barrier layer.

As shown in FIG. 11*a*, the second layer 919 is a one-time breakable element extending between the first barrier layer 916*a* and the second barrier layer 916*b*. The one-time breakable element of the second layer 919 therefore inhibits or prevents the odor management agent from escaping into the package while in its initial position shown in FIG. 11*a*.

The one-time breakable element 921 can include one or more polymeric resins and polyolefins, and can be used with any of the previously-described odor management structures. Polyolefins used as one-time breakable element include, but are not limited to, polyethylenes, polypropylenes, and combinations thereof. Some non-limiting types of polyethylenes include low density polyethylenes (LDPE), linear low density polyethylenes (LLDPE), high density polyethylenes (HDPE), medium density polyethylenes (MDPE) and combinations thereof. Other non-limiting examples include plastomers, elastomers, ethylene vinyl acetates (EVA), ethyl methacrylates, polymethylpentene copolymers, polyisobutylenes, polyolefin ionomers, cyclic olefin copolymers (COCs), or combinations thereof, including with polyethylenes and/or polypropylenes.

The one-time breakable element of the second layer 919 can include a one-time breakable preferential area of weakness or preferential tear area similar to the preferential areas of weakness or tear areas previously described herein or a one-time breakable adhesive or cohesive seal. Alternatively, the second layer 919 can be formed by selectively cross-linking the diffusion material to define the one-time breakable element. Generally, the bond between the second layer 919 and the adjacent layers must be stronger than the frangible portion of the one-time breakable element that joins portions 919*a* and 919*b* as described further below.

Figure 11B:
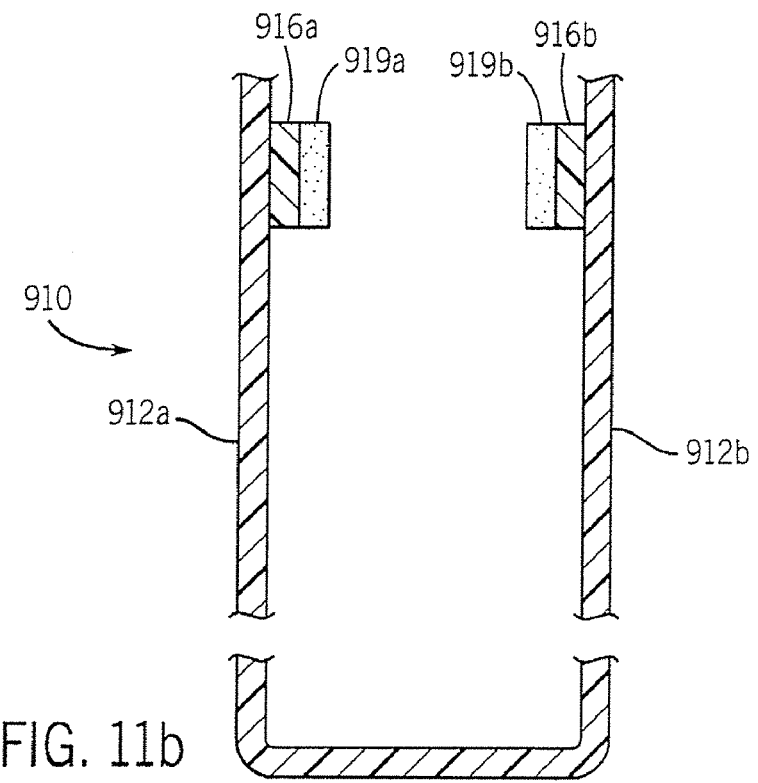
FIG. 11b is a partial cross-section view showing the reclosable package or bag of FIG. 11a after breakage of the one-time breakable element.

As shown in FIG. 11*b*, breakage of the one-time breakable element divides the second layer 919 into a first portion 919*a* and a second portion 919*b*, each having a surface exposed, and thereby begins or enhances the release of odor management agent thereto. Typically, breakage of the one-time breakable element by a user occurs when the package is initially opened to place contents therein.

Figure 12A:
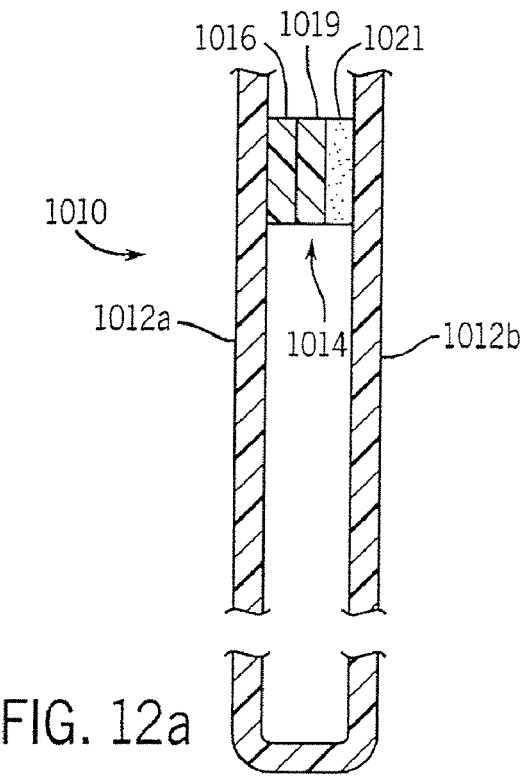
FIG. 12a is a partial cross-section view of two sides of a reclosable package or bag, in which one side includes a polymeric structure that comprises two layers, and in which the polymeric structure is connected to the other side by a removable element.

In another such embodiment having a mechanical release mechanism, a reclosable package 1010, made from a web material in accordance with the invention, is shown in FIG. 12*a* comprising a first thermoplastic body panel 1012*a*, a second thermoplastic body panel 1012*b*, an odor management structure 1014, and a removable or peelable cover 1021. The first and second body panels 1012*a*, 1012*b* are joined along a pair of opposing sides and a bottom bridging the sides so as to form an open mouth. The joined first and second body panels form an interior space for storing items. The odor management structure 1014 is in the form of a patch or tape and comprises two layers, e.g., a first layer 1016 being a barrier layer and a second polymeric layer 1019 being a diffusion layer and including an odor management agent.

Figure 12B:
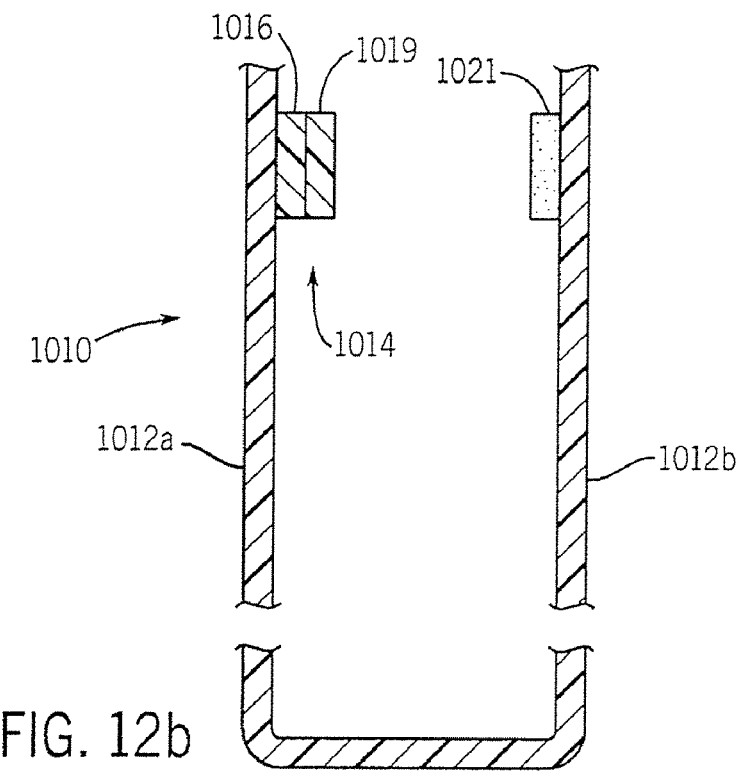
FIG. 12b is a partial cross-section view showing the reclosable package or bag of FIG. 12a after removal of the removable element.

As shown in FIG. 12*a*, the removable cover 1021 is similar to that of FIG. 8, but is securely attached to panel 1012*b*. The removable cover 1021 covers at least a portion of the second layer 1019, and, as shown, preferably covers the entire second layer 1019 that is otherwise exposed in the interior of the package 1010. As shown in FIG. 12*b*, removal of the cover 1021 exposes the odor management layer 1019 to the interior of the package 1010 and thereby begins or enhances release of odor management agent thereto at least while the package is open. This embodiment of FIGS. 12*a* and 12*b* is particularly suitable for waste bags and liners or the like.

Alternatively, in some embodiments, the removable cover 1021 can cooperate with a slider of the fastener of the reclosable package 1010, so that the removable cover can be removed from the odor management layer when the reclosable package 1010 is opened via the slider.

As set forth above, the subject web material can be used in processes to form the foregoing reclosable containers. The web material is used as a film to construct the body panels, or walls of the foregoing reclosable packages. The web material is either manufactured in a separate manufacturing process, or in-line with and preceding forming of containers with the web material. These containers include, but are not limited to rigid containers, bags, wraps and foils. The previous exemplary embodiments are directed to a web material including a first layer having an active agent carried thereon by an agent structure. Reference will now be made to alternative web material constructions of the invention.

Figure 13:
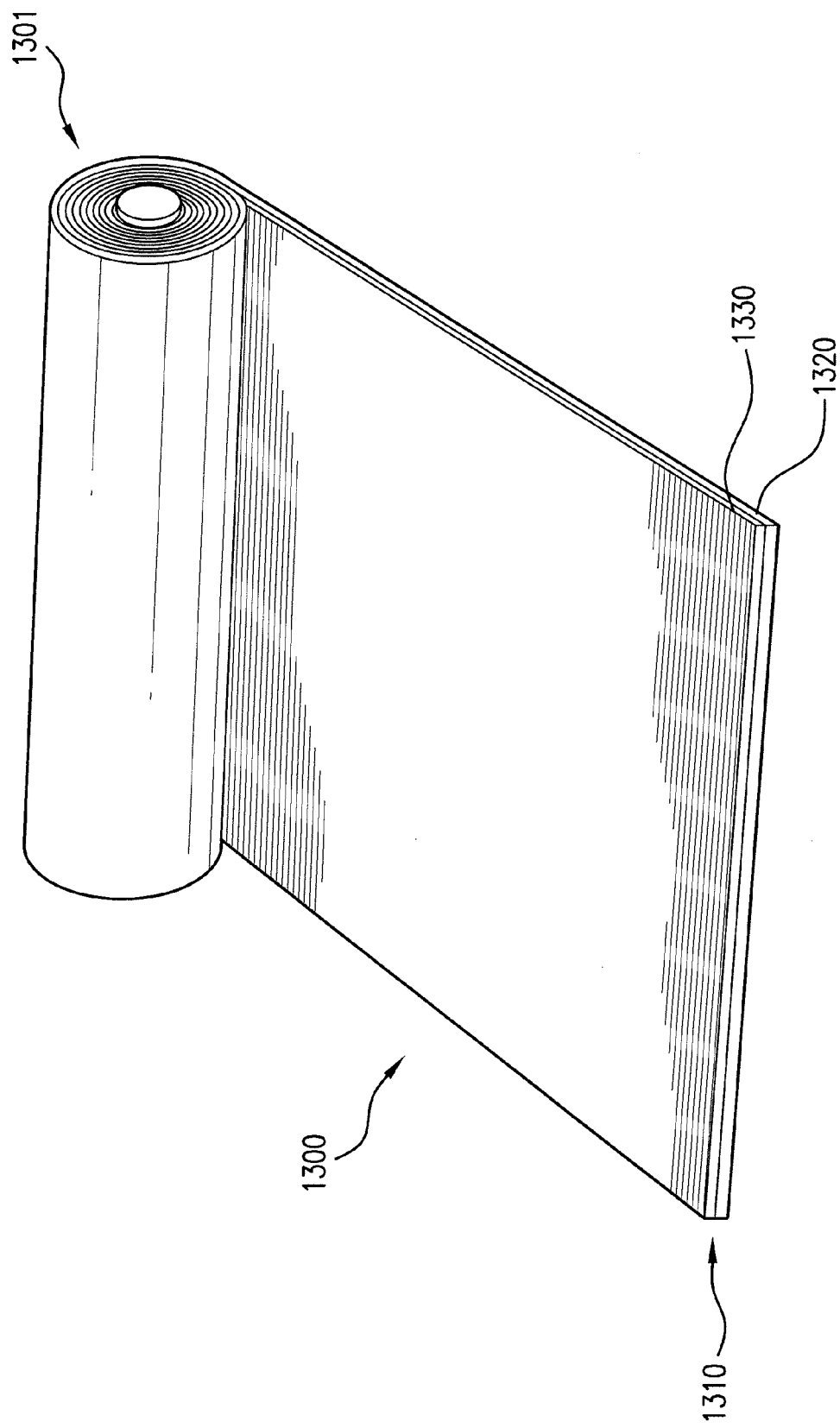
FIG. 13 is an isometric view of one embodiment of a web material web material in accordance with the invention, including a two-layer structure.

FIG. 13 illustrates a web material 1300 in accordance with another aspect of the invention. As illustrated, the web material 1300 is disposed in a roll 1301, and includes two layers 1320 and 1330, joined along an interface 1310. As embodied herein, the first layer 1320 preferably acts as a barrier layer and the second layer 1330 preferably acts as a diffusion layer. Active agents, can be disposed either within the second layer 1330, or between the first layer 1320 and the second layer 1330. The first layer 1320, as a barrier layer, preferably inhibits passage of water and active agent, while the second layer 1330, as a diffusion layer, allows passage of at least active agent vapor. Depending on the intended use, permeability to both water vapor and active agent vapor is desired through the second layer. In certain embodiments, the diffusion layer not only is permeable to water vapor but is hydrophilic. If desired, an increased resistance to diffusion through the barrier layer can be achieved by increasing the thickness of the barrier layer. By contrast, and as set forth above, inhibition of the passage of solid, liquid and vapor phases of water and active agent through the barrier layer is desirable. Any of the barrier and diffusion materials set forth herein, or other suitable materials can be utilized. In a preferred embodiment, the barrier materials include polypropylene (PP) or polyethylene terephthalate (PET), and the diffusion materials include polymers such as ethylene methyl acrylate (EMA), ethylene vinyl-acetate (EVA) or Nylon, for example.

The web material of FIG. 13 advantageously releases active agent from the surface of the second layer, which can be aligned with or positioned adjacent the food or other perishable product. This feature is advantageous regardless of the form of the web material e.g., a wrap, material or bag. Furthermore, and in accordance with another aspect of the invention, the second material layer has a predetermined material property. For example, if intended for use as a food wrap, it is preferable that the diffusion layer embodied herein include cling characteristics, such as through inclusion or use of one or more cling materials. Preferably, a cling material is capable of being attracted to and/or adhering at least to glass or metal containers. If intended for use as a lidding material, the diffusion layer should be capable of sealing to other plastic materials. In such embodiments, a material can be selected to include a predetermined material property that performs the desired function. Preferably, the material is still permeable to both water vapor and active agent, to allow water vapor to activate the active agent, and to allow the active agent to enter the compartment of the package.

Cling materials can include a material selected from the group consisting of linear low density polyethylene, linear ultra low density polyethylene, polyethylene copolymer, ethylene-.alpha.-olefin copolymer, polyisobutylene, atactic polypropylene, cis-polybutadiene, bromobutyl rubber, ethylene vinyl acetate (EVA), ethyl methyl acetate (EMA), and combinations thereof. Selected cling materials are set forth in U.S. Pat. No. 4,624,991, U.S. Pat. No. 6,500,901, U.S. Pat. No. RE38,658, U.S. Pat. No. 4,348,455, U.S. Pat. No. 5,334,428, U.S. Pat. No. 6,083,611, and U.S. Pat. No. 4,430,457, each of which is incorporated herein in its entirety.

If the web material is embodied as a lidding material, the web material can include, but need not be limited to metal foils, polyethylene terephthalate, Nylon, metallized polymers, polyvinylidene chloride, and ethylene vinyl alcohol.

Figure 14:
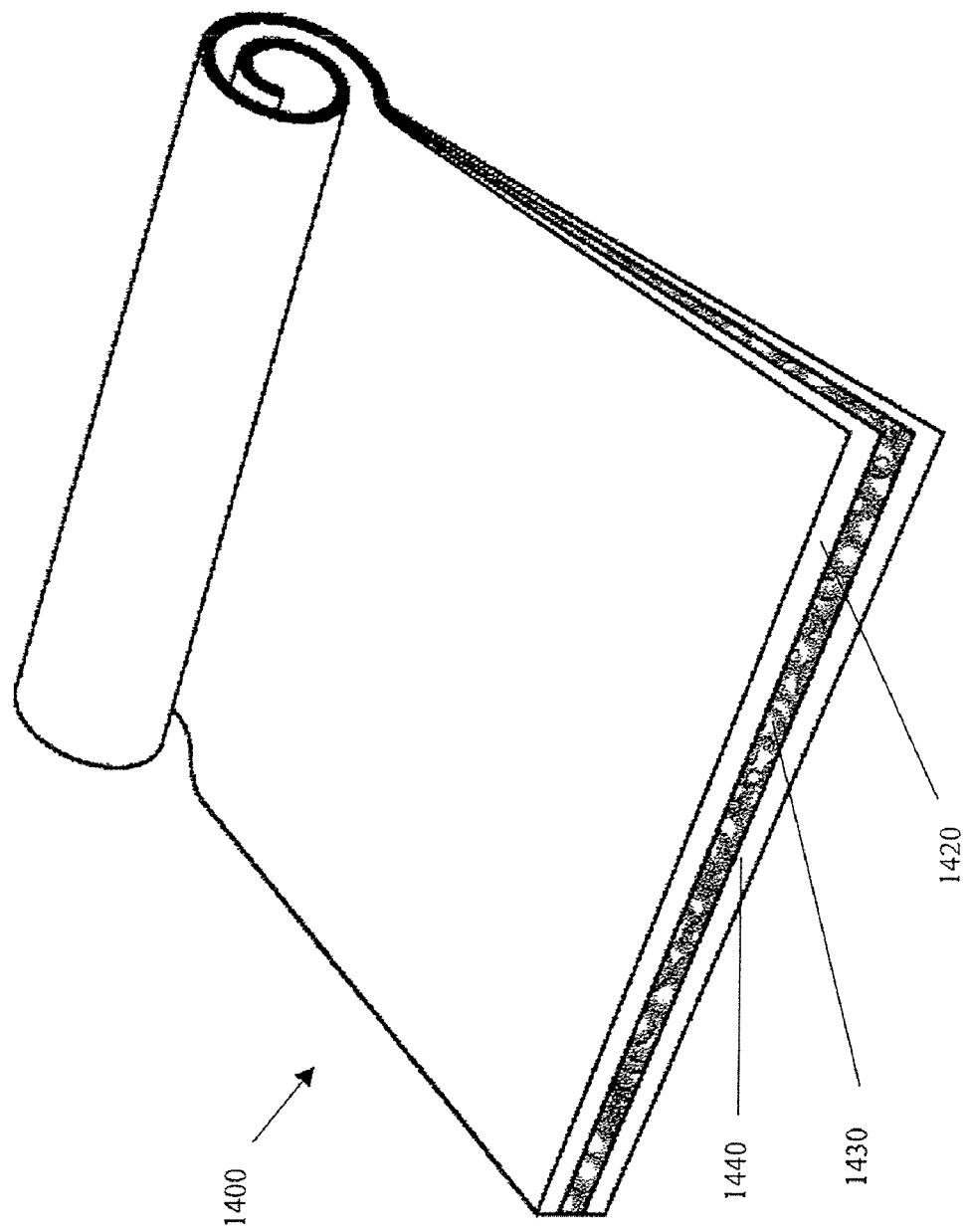
FIG. 14 is an isometric view of another embodiment of a web material in accordance with the invention, including a three-layer structure.

Further in accordance with the invention, a web material can include at least three material layers. FIG. 14 illustrates a web material 1400 similar to the web material 1300 of FIG. 13, but one which includes three such material layers. The web material includes a first material layer 1440, which is preferably a barrier layer, a second material layer 1430, which is preferably an active agent layer, and a third material layer 1420, which is preferably a functional layer 1420. At least one of either the active agent layer 1430 or the functional layer preferably acts as a diffusion layer, allowing passage of water and active agent vapor. The functional layer 1420 has a predetermined material property, such as providing cling and/or sealing characteristics, but also should be permeable to active agent vapor. Accordingly, a material for the functional layer 1420 that both provides the predetermined material property and is suitable for use as a diffusion layer for active agent vapor and water vapor, is desirable. Advantageously, the amount of functional layer can be reduced as compared with that incorporated with the embodiment of FIG. 13.

In the embodiments of FIGS. 13 and 14, the plurality of layers can be co-extruded during manufacture, or can be mutually attached following extrusion. Mutual attachment can be achieved in any suitable manner and can include spraying, dipping, static adhesion, printing, co-extrusion, electroless deposition, casting, vapor deposition, fusion, and/or embedding, among other processes. Further, the layers can be coextensive, or certain layers can extend further than other layers. Other variations and modifications are described in further detail. The amount and rate of active agent released from the web material can be controlled by adjusting the concentration of active agent and/or the diffusing characteristics of the diffusion layer.

In accordance with another aspect, the invention includes a web material disposed in the form of a stripe on the first material layer. FIGS. 15 and 16 illustrate isometric and end views, respectively, of a web material 1500, wherein a first layer 1510 and a second layer 1530 are provided, and wherein active agent is disposed in the form of a stripe 1540. The stripe can be incorporated in one of the first and second layers, or disposed between the first and second layers as depicted in FIG. 16. As set forth above, at least one of the first layer 1510 and the second layer 1530 embodied herein is a barrier layer, the other being a diffusion layer, permeable to at least active agent vapor. As set forth hereinabove, water vapor can act to initiate the release of active agent; therefore, the diffusion layer is also preferably permeable to water vapor. The width of the stripe 1540 therefore can be preselected so as to provide the desired amount of active agent at a desired location. The width of the stripe can range from a thin line to a layer that extends substantially across the entire with of the web material. As such, a range of amounts of active agent can be incorporated, thereby tailoring the amount of active agent released from the web material. If more active agent is desired, for example, then a wider stripe 1540 can be applied. If less is desired, a narrower stripe 1540 can be provided. Likewise, the location of active agent can be controlled by the location of the stripe. The relative amount of coverage provided by the stripe 1540 is referred to herein as the "active agent area." As evident in the descriptions that follow, the active agent area is not limited to a straight line or stripe, but can include alternative configurations, including a pattern for the application of active agent in accordance with the invention. In a pattern, the active agent need not cover the entire region to which it is applied, and therefore, allows further tailoring of the available active agent, as appropriate.

Figure 17:
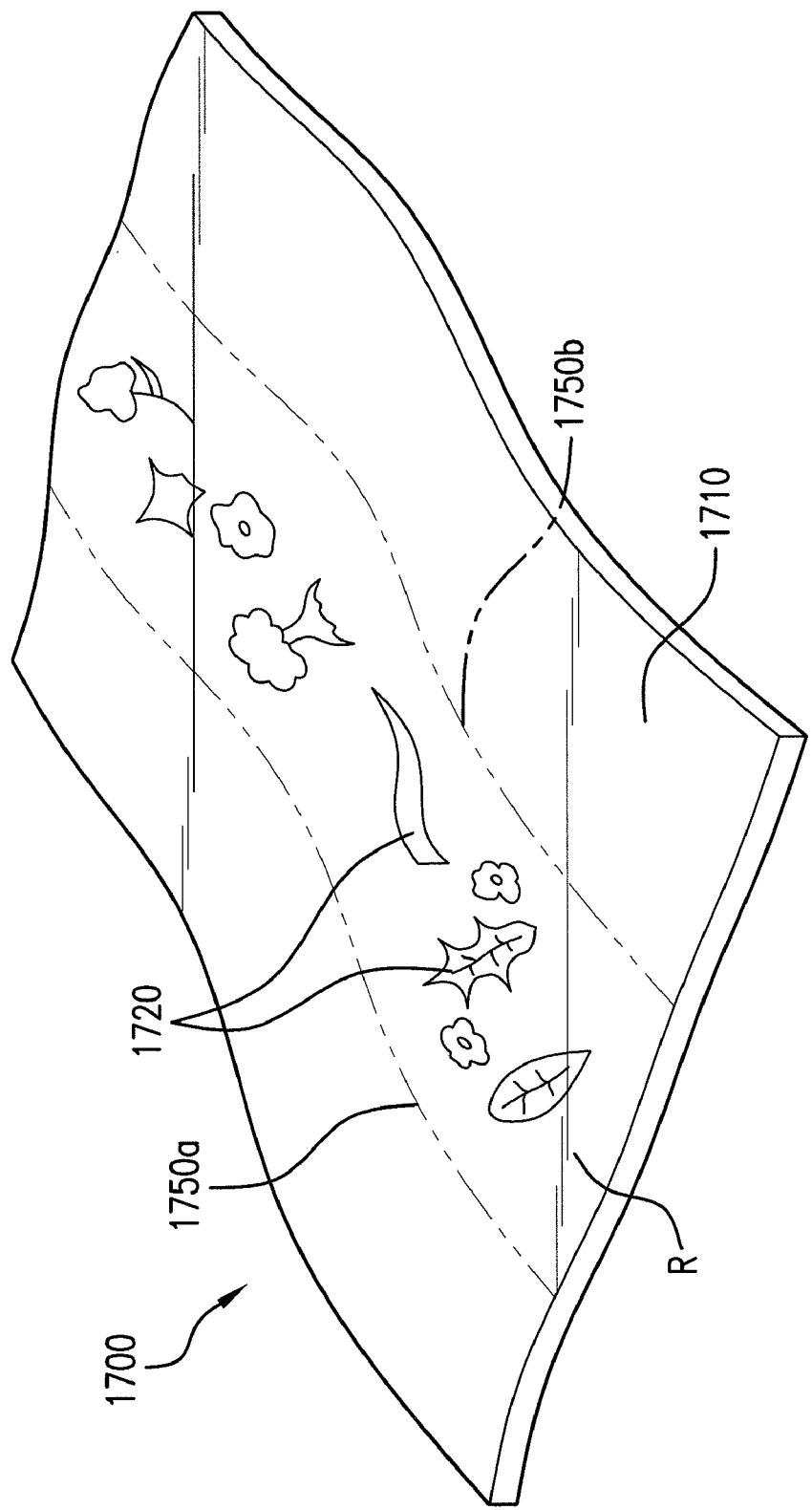
FIG. 17 is an isometric view of another embodiment of a web material in accordance with the invention, including active agent applied in a pattern.

FIG. 17 illustrates a web material 1700 in accordance with the invention, wherein active agent is disposed in a pattern 1720 on a material web 1710. The material web can be any suitable material, but preferably includes a barrier material. Additionally, the material web 1710 can include at least one predetermined material property to provide features such as cling or sealing capability. In the embodiment illustrated, the pattern 1720 is confined by borders 1750a and 1750b, which define an active agent region R. In this embodiment, active agent is only applied as part of the pattern. As is apparent from the figure, the active agent area can be reduced when the active agent is disposed in a pattern. The active agent can be applied in any of an endless variety of patterns by way of, e.g. printing plates, roller(s), brush(es), or ink jet. In certain embodiments, the active agent is disposed in conjunction with color indicators. Such indicators can also be applied in a pattern together with or separate from the active agent. Further, the pattern and/or any other mode of presenting the active agent, can include colorants to provide a desired aesthetic effect. Accordingly, if desired, color images can be provided, with such images also carrying active agent.

Figure 18:
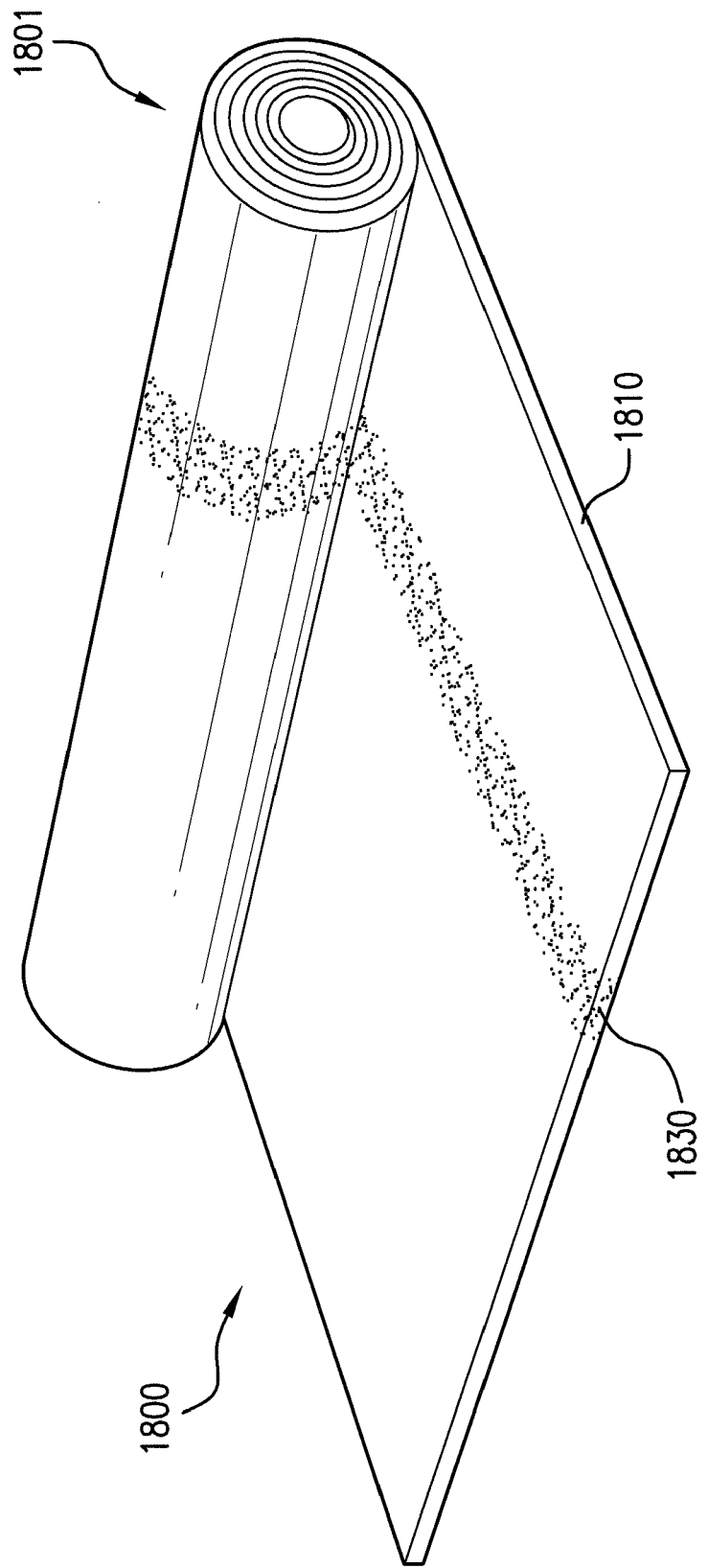
FIG. 18 is an isometric view of another embodiment of a web material in accordance with the invention, including active agent incorporated into a portion of the web material.

As an alternative to the embodiment of FIG. 15, FIG. 18 illustrates a web material 1800, in accordance with the invention in which active agent 1830 is carried by the first material layer 1810 of the web material 1800, which itself is provided in a roll 1801. In accordance with the invention, the web material includes a first layer, which is preferably a barrier material, and an active agent carried by the first material layer. As embodied herein, and as depicted in FIG. 18, the active agent is preferably disposed in the form of a stripe. Alternatively, the active agent can be incorporated into the web material. In this embodiment, it is desirable to use a material for the first material layer 1810 that is permeable to the active agent, so that once activated, the active agent vapor can be released from the web material 1800. Accordingly, materials suitable for use as diffusion materials are preferred, at least for the portion of the web material 1800 that contains active agent 1830. To inhibit the activation and release of active agent into the surrounding environment, the embodiment of FIG. 18 can be paired with a barrier material. The barrier material can be laminated or co-extruded with the first material layer 1810 to form a further web material, for example, a wrap material or lid stock, depending on the materials selected.

The first material layer 1810 can be extruded with the active agent 1830 illustrated, in one co-extrusion step. A modular die can be used for this purpose, such as those found, for example, in U.S. Pat. Nos. 5,762,971, 6,413,595 and 6,000,926. The active agent can be premixed with the material used for the first material layer 1810, in the region of the die designated for extrusion of the active agent strip 1830 or simply injected into that portion of the extrusion die. Further, the web material 1800 can be provided with a removable release liner, as described below, such as waxed paper, to prevent premature release of active agent therefrom, prior to use. Once drawn from the roll 1801, such removable release liner may be removed to allow active agent to be released. Accordingly, a release liner having sufficient barrier properties is preferred.

Figure 19:
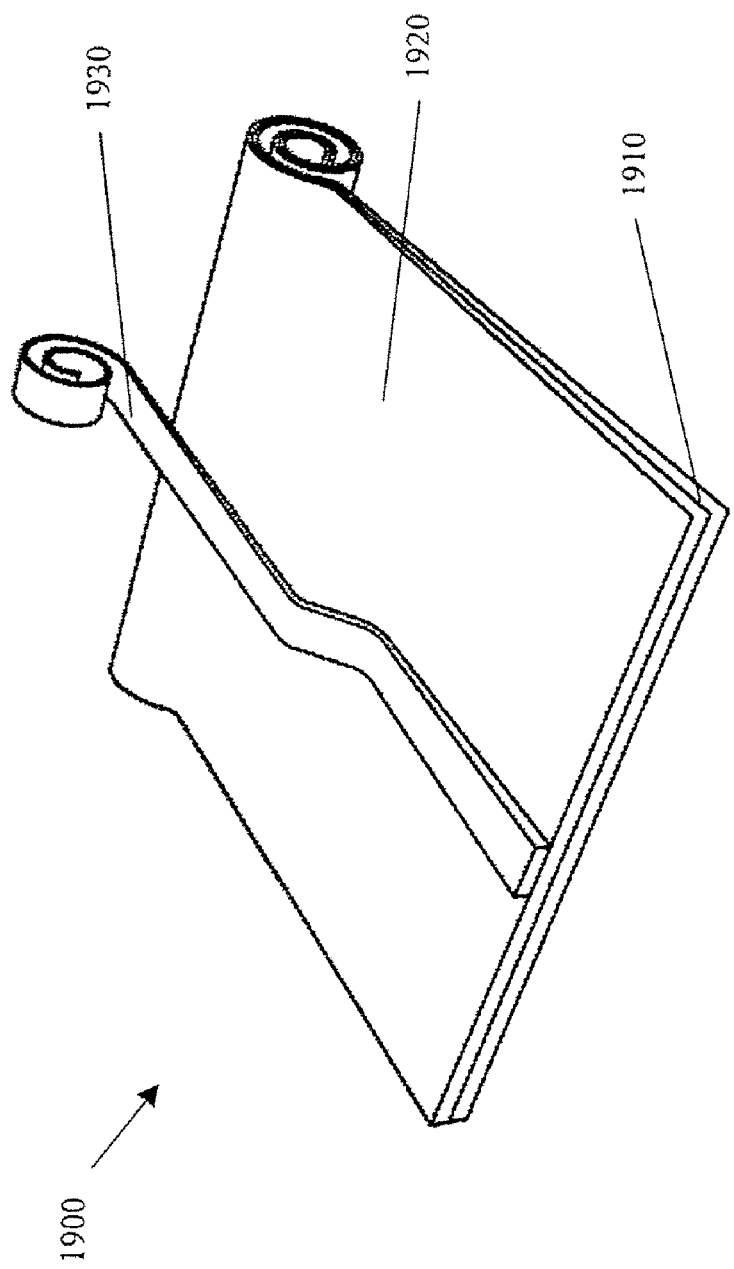
FIG. 19 is an isometric view of another embodiment of a web material in accordance with the invention, including active agent applied as a stripe to a base layer of the web material.

In accordance with another aspect of the invention, FIG. 19 illustrates a web material 1900 wherein a stripe of active agent material in the form of a tape 1930 is applied to a surface of a base material web 1920. The web material 1900 can then be processed by any number of subsequent steps or techniques. The web material 1900 can be formed into a package, such as a bag, heat sealing edges and attaching reclosable fasteners, if desired. Alternatively, the web material can be prepared further by incorporating additional material layers, such as a material layer with predetermined material properties, including permeability, cling or sealing characteristics. Alternatively or additionally, a removable cover or covers can be applied for selective activation of the active agent.

The material web 1920 can have a plurality of layers joined along an interface, such as interface 1910, although a single layer can be used if desired. The materials for the web material 1900 preferably include at least one barrier layer. Further, the tape preferably includes properties of a diffusion layer to allow passage of active agent therefrom. The tape 1930, which contains active agent, can be applied via an adhesive, heat seal, sonic weld or other attachment technique, such as those set forth herein. Alternatively, the tape 1930 can be extruded concurrently with the material web 1920, and joined thereto during or after forming.

The web materials having active agents, e.g. odor management structures incorporated therewith of the present invention, if disposed as a patch, tape, or pouch, can be attached to a package such as a reclosable bag by a pressure-sensitive self-adhesive. The pressure-sensitive self-adhesive can be any suitable adhesive that affixes the odor management structure to the reclosable package. Non-limiting examples of suitable pressure-sensitive adhesives include acrylic or rubber-based adhesives. While a pouch of antimicrobial agent can be utilized in certain embodiments, relatively flat web materials are preferred.

When provided in the form of a tape or patch, the odor management structure can be roll fed onto a layer(s) of the web material, as shown in FIG. 19. The roll-fed odor management structure can initially include a release liner to assist in proper placement of the odor management structure. The release liner, if used, is separated from the roll-fed odor management structure before the tape or patch is attached to the reclosable web material. Examples of release liners include silicon-coated paper. Alternatively, the odor management structure can be roll fed without the use of a release liner before being attached to the web material, if desired. Furthermore, the odor management structure can be magazine fed during attachment to the reclosable package.

According to another embodiment, the odor management structure patch, tape, or pouch can be heat sealed or welded directly to the web material. For example, the odor management structure can be roll fed or magazine fed before being heat sealed or welded to the reclosable package. In a heat-sealing embodiment, a release liner would not be needed. The odor management structure can be attached continually to the web material, or at selected locations, if desired. Alternatively, the odor management structure can be attached to the body panels during the formation of the package. For example, the odor management structure can extend between the side seals formed between the first and second body panels so as to be secured by the side seals. It is contemplated that other attaching methods can be used.

Figure 20:
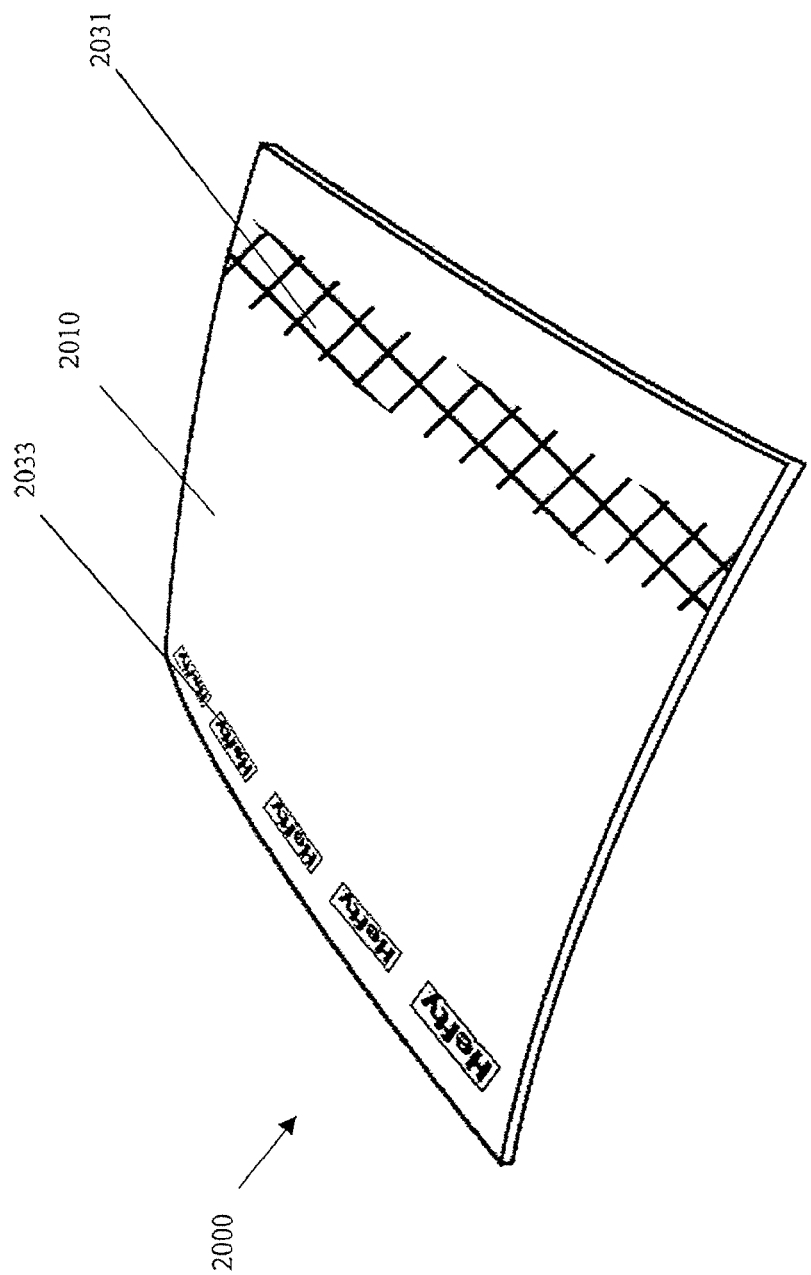
FIG. 20 is an isometric view of another embodiment of a web material in accordance with the invention, including active agent applied in a pattern.

FIG. 20 is an isometric view of another embodiment of a web material 2000 in accordance with another aspect of the invention, including active agent applied in a pattern 2031, 2033 to a base layer. The pattern 2032, 2033 can be applied to the base material web 2010 by any suitable mode, such as those set forth herein. For example, a repetitive printed pattern, such as the logo 2033 or cross-hatch 2031 can be printed by way of plates, while a pattern such as an expiration date, brand name, product contents or other changeable text, can be printed by way of an inkjet. If desired, active agent can be disposed in the form of printed text. Moreover, a color indicator, such as those described herein, can be utilized, further enhancing the functionality of a package. As with other web materials described herein, the web material 2000 can be used to form any of a variety of items, including wraps, lid stock and bags. In accordance with the invention, any suitable material, such as those set forth above, can be used to form the web material 2000. Preferably, the material web 2010 of the web material 2000, on which the active agent is applied, is a barrier material so that the active agent is not released inadvertently or leaked through a wall of a package.

Figure 21:
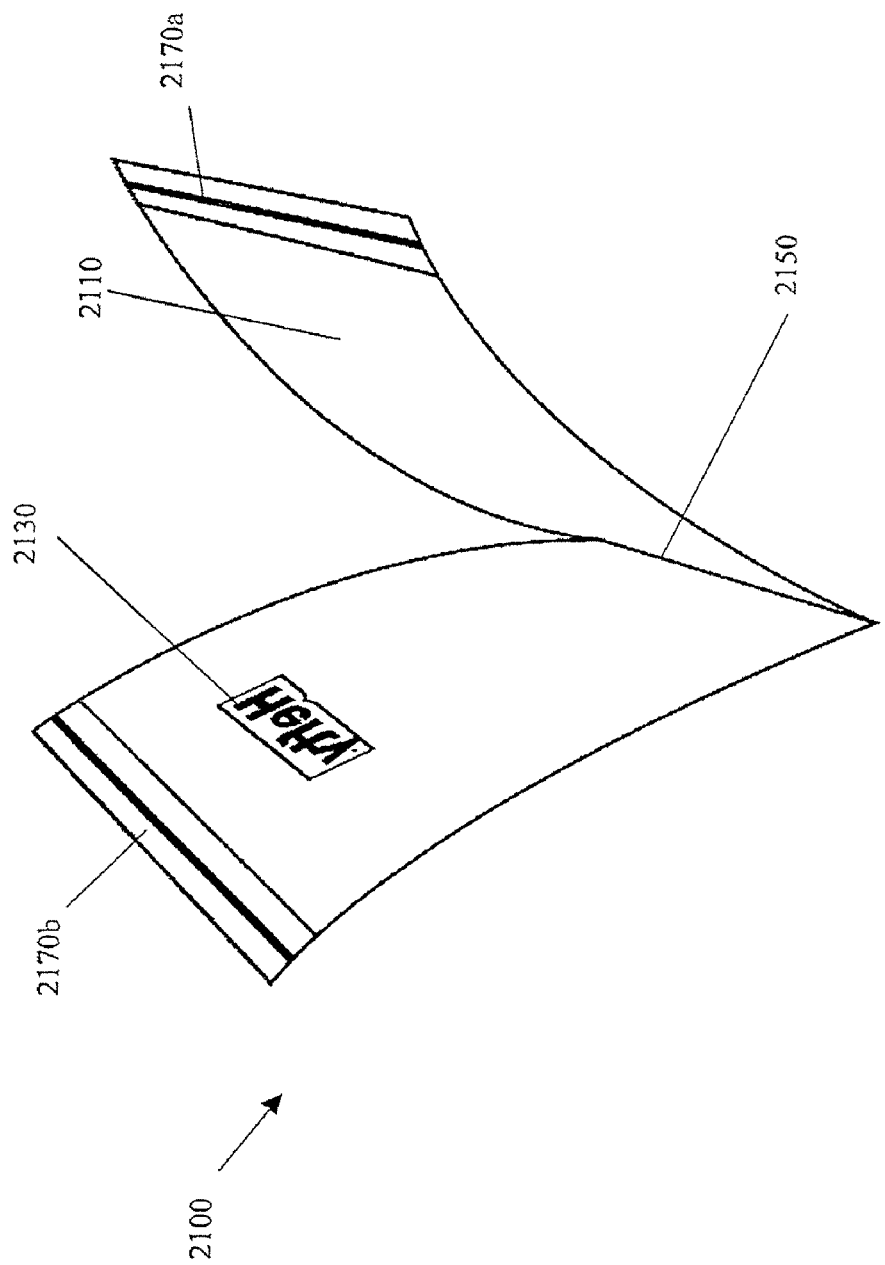
FIG. 21 is an isometric view of another embodiment of a web material in accordance with the invention, wherein the web material is being formed into a reclosable bag.

FIG. 21 is an isometric view of another embodiment of a web material in accordance with the invention, illustrating a partially exploded view of a reclosable bag 2100 formed from the web material 2110. As shown, a logo 2130 is disposed on a body panel of the bag 2100. The bag 2100 can be made from one web material 2110, folded along a crease 2150, or can be formed from a plurality of distinct web materials, such as a first web material having an active agent, and a second web material with or without active agent. As with the embodiment of FIG. 20, the logo 2130 can include active agent therein, and can be applied to the web material 2110 by way of printing, for example. Alternatively, the logo 2130 can be disposed on a patch, in any of the embodiments described above, with the patch attached to the web material 2110 prior to forming the web material 2110 into the reclosable bag 2100. Preferably, such patches are applied to the web material 2110 at regular intervals which allows the patches ultimately to be disposed in individual bags or packages once the packages are formed from the web material 2110. Further, reclosable fastener portions 2170*a*, 2170*b* are applied to the web material 2110, if desired, and the body panels made of the web material 2110 are sealed and thereby formed into the final bag.

The reclosable packages, such as reclosable bag 2100 or reclosable package 10 (FIG. 1), can be formed of any suitable material, such as by a thermoplastic material suitable for storing or collecting items, including perishables storage. Examples include common-sized reclosable packages such as pint storage and freezer bags, quart storage and freezer bags, and gallon storage and freezer bags. The reclosable packages are typically formed from polymeric materials such as polyolefinic materials. Non-limiting examples of polyolefinic materials include polyethylenes, polypropylenes, polystyrene, and combinations thereof. For example, some types of polyethylenes materials include high density polyethylenes (HDPE), low density polyethylenes (LDPE), linear low density polyethylenes (LLDPE), and combinations thereof. It is also contemplated that materials such as plastomers, elastomers, ethylene vinyl acetates (EVA), ethyl methacrylates, polymethylpentene copolymers, polyisobutylenes, polyolefin ionomers, cyclic olefin copolymers (COCs) or combinations thereof, including polyethylenes, and/or polypropylenes may be used in forming the reclosable packages of the present invention. The thicknesses of the reclosable packages can vary in the present invention, but are generally from about 0.5 mil to about 5 mils and, more specifically, from about 1 mil to about 3 mils.

As previously described herein, the odor management agents of the present invention can be used in combination with a web material for use in forming a body panel of a package. Alternatively and/or in combination, the odor management agents of the present invention can be used in combination with fin portions of a fastener of a reclosable package, as further described in co-pending U.S. patent application Ser. No. 11/055,574, the contents of which application are expressly incorporated by reference herein in its entirety.

Figure 22:
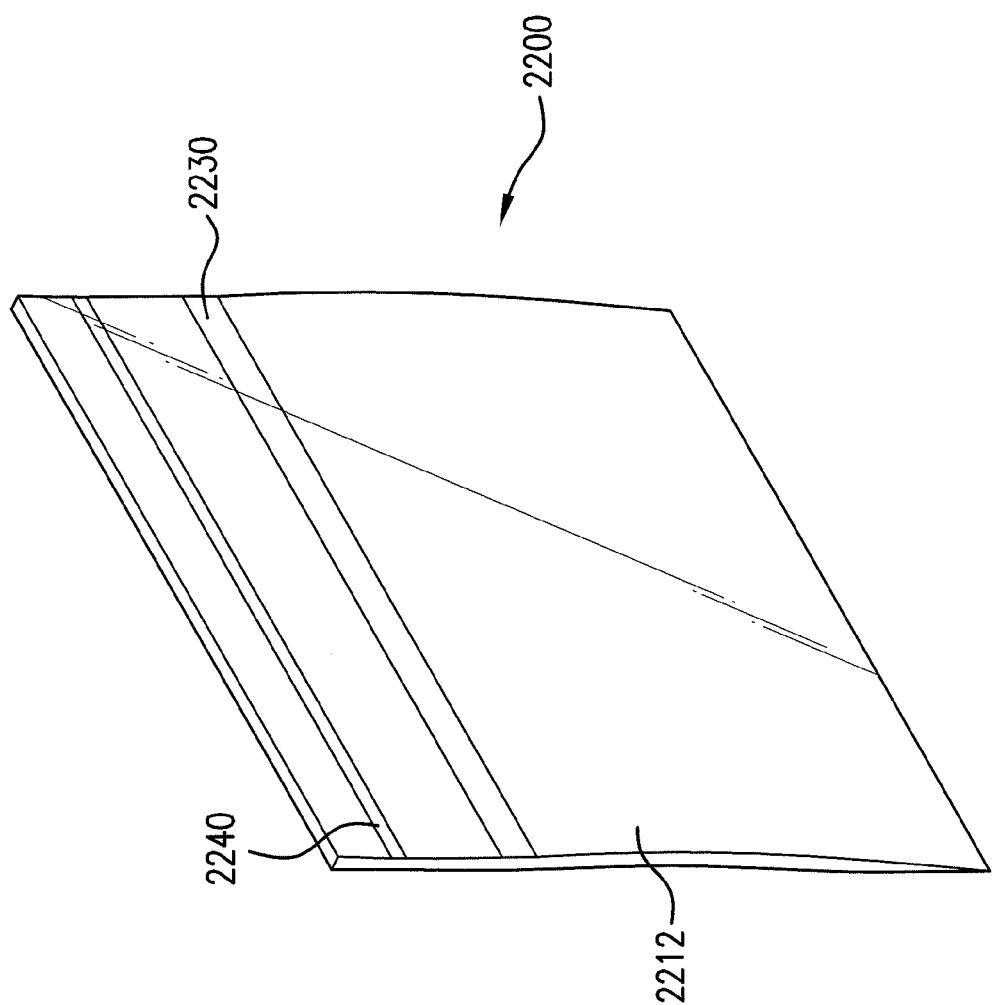
FIG. 22 is an isometric view of another embodiment of a web material in accordance with the invention, wherein the web material with a stripe of active agent has been formed into a reclosable bag.

FIG. 22 is an isometric view of preferred embodiment of a web material in accordance with the invention, wherein the web material 2212 with a stripe 2230 of active agent has been formed into a reclosable bag 2200. The web material can include any of the features and materials of construction described herein. As embodied, a reclosable fastener 2240 is provided, and the stripe 2230 extends the entire width of the bag 2200, preferably proximate the mouth of the bag. The web material 2212 used for forming this bag 2200 can include any of those set forth herein, such as web materials 1500, 1700, 1800, 1900, 2000 and 2300, for example.

Figure 23:
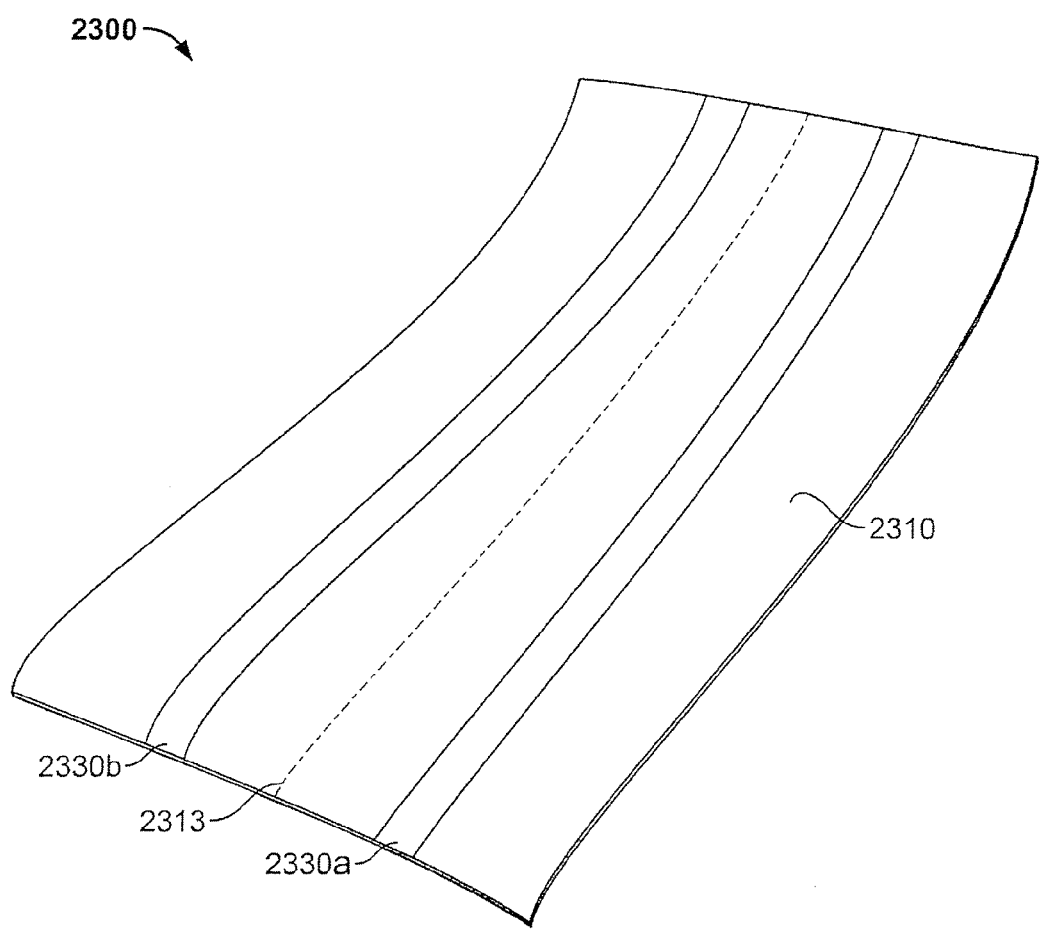
FIG. 23 is an isometric view of another embodiment of a web material in accordance with the invention, wherein the web material includes a plurality of stripes of active agent.

FIG. 23 is an isometric view of another embodiment of a web material in accordance with the invention, wherein the web material 2300 includes a plurality of stripes 2330a, 2330b of active agent provided on a base material 2310. As with the embodiments of FIGS. 9a, 9b, 10a, 10b, 10c, 11b and 12b, the active agent can be provided in a plurality of portions. Stripes 2330a, 2330b generally are aligned together when the web material 2300 is folded along line 2313 during manufacture. Any of the features set forth herein can be applied to the web material 2300, particularly the features described in connection with FIGS. 9a, 9b, 10a, 10b, 10c, 11b and 12b.

Alternatively, the web material 2300 can be formed into a wrap or lidding material, and not folded along line 2313. When embodied as a wrap or lidding material, a functional layer (e.g., a sealable layer or cling layer) can be disposed adjacent the base material 2310 and stripes 2330a, 2330b. As with similar foregoing embodiments, the functional layer preferably is permeable to active agent vapor to allow release of the active agent from the web material. Alternatively, the base material and stripes 2330a, 2330b can provide such function, if constructed from appropriate materials.

Figure 24:
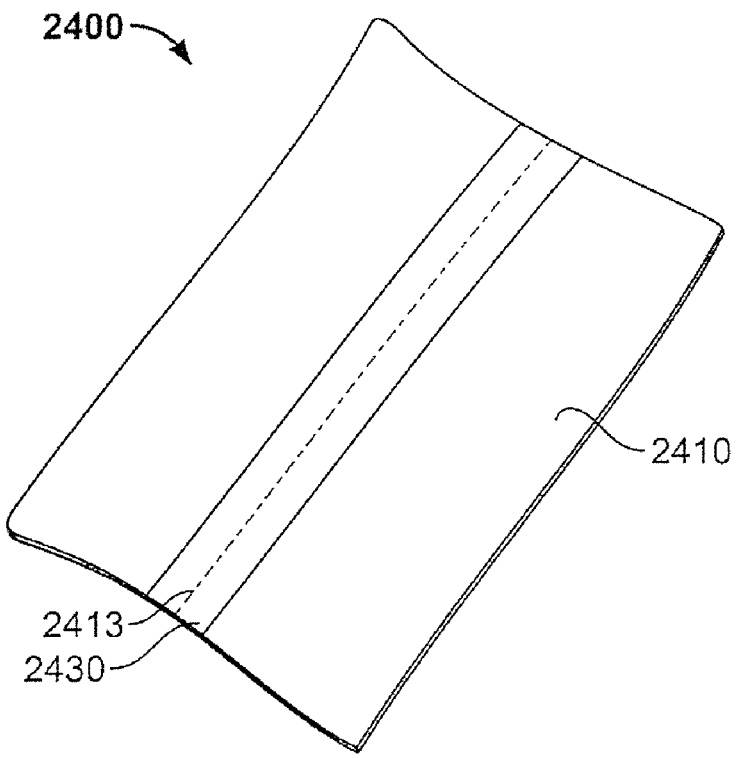
FIG. 24 is an isometric view of another embodiment of a web material in accordance with the invention, wherein the web material includes a central stripe of active agent.
Figure 25:
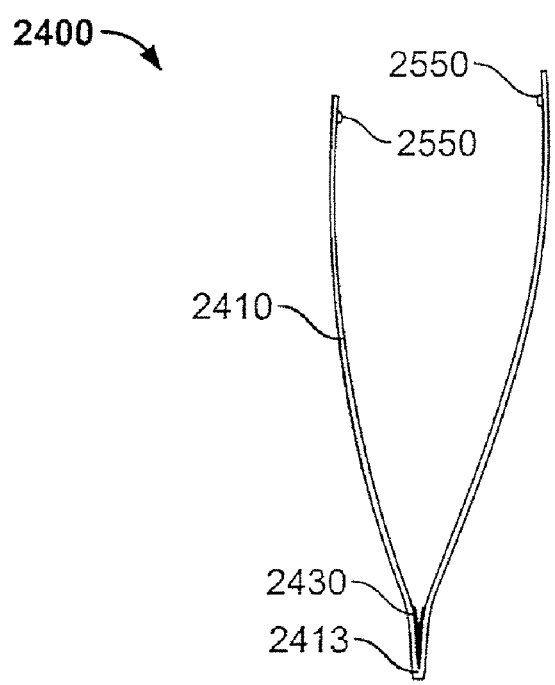
FIG. 25 is an end view of a reclosable bag formed by the web material of FIG. 24.

FIGS. 24 and 25 are isometric and end views of another embodiment of a web material in accordance with the invention, wherein the web material 2400 includes a centrally oriented stripe 2430 of active agent. As with the foregoing embodiment, the web material 2400 can be folded along a center line 2413. Both the active agent stripe 2430 and reclosable fastener 2550 can be attached to the base web material 2410 or formed integrally therewith. Alternatively, as with each embodiment herein, the active agent can be incorporated in the web material 2410. A bag formed by this embodiment of the web material 2400 can be used, for example, in situations where an inconspicuous placement of active agent at the bottom of the bag is desirable. Moreover, features set forth hereinabove in connection with other embodiments can be applied to this embodiment.

Figure 26:
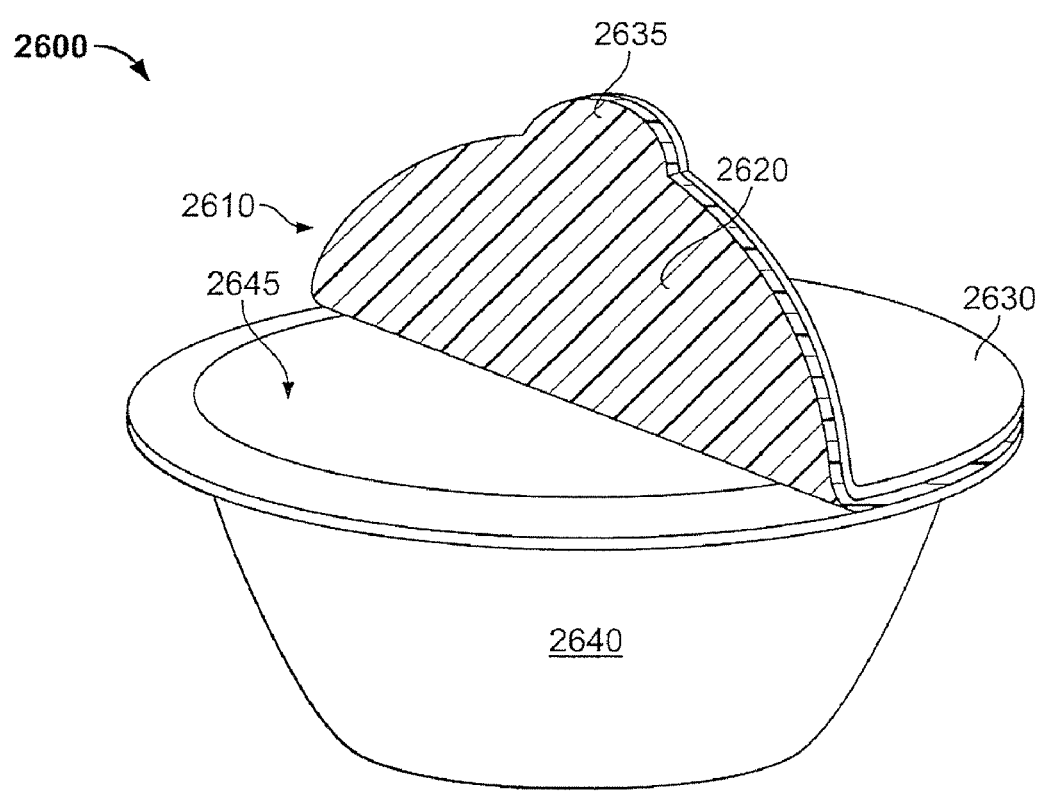
FIG. 26 is an isometric view of another embodiment of a web material in accordance with the invention, wherein the web material having active agent is a lidding material.

FIG. 26 is an isometric view of a container 2600, which incorporates another embodiment of a web material in accordance with the invention, wherein the web material 2610 is a lidding material for application to a base or receptacle 2640. As set forth above, for example as in connection with the embodiments of FIGS. 13 and 14, the lidding material can include two or more layers, wherein the layer most adjacent to the receptacle 2640 is capable of being sealed thereto. The lowermost layer 2620 preferably is permeable to active agent vapor to allow the release of active agent into receptacle space 2645 of the package. Suitable materials, as previously described, allow relatively easy removal from the receptacle 2640, when removal is desired. The outermost layer is preferably a barrier material selected from those set forth hereinabove.

For purposes of additional illustration, disclosed bags or liners of the present invention will now further be described herein with respect to odor management agents incorporated in or carried by agent structures of the invention.

A bag of the invention was produced by using a masterbatch formulation of the odor management agent. A masterbatch formulation was obtained from the International Fragrance and Flavor Company ("IFF", New York, N.Y.). The masterbatch included an odor management agent having a counteractant agent that included a Veilex™ cyclohexyl compound and a neutralizing agent that included TegoSorb 50™, a zinc ricinoleate compound, formulated in a specific relative ratio. The TegoSorb 50™ was loaded in an oil-based carrier at 25% (wt). In the TegoSorb 50™ concentrate, zinc ricinoleate was present at 50% (wt), making the level of zinc ricinoleate in the oil-based carrier 12.5% (wt). The oil carrying the odor management agent was then added at 25% (wt) to a compounding extruder and compounded with a polymer to make the carrier polymer masterbatch. The masterbatch carrier polymer was then added over a range of 1% to 4% (wt) to a matrix polymer. The masterbatch carrier polymer was mixed and melted with a matrix polymer resin of liner low density polyethylene (Dow Chemical, MI=0.9) at a 450° F. die temperature. The molten polymer mixture was extruded through a tubular blown extruder device to make 0.9 mil webs having the odor management agent dispersed therethrough. As a result, when the masterbatch carrier polymer was added to the matrix polymer over the range of 1% to 4%, the level of the TegoSorb 50™ in the web ranged 0.0625% to 0.250% (wt), or 625 ppm to 2500 ppm, and the level of Veilex™ counteractant in the web ranged from 0.05% to 5.0% (wt), or 500 ppm to 50,000 ppm. One of ordinary skill in the art will appreciate that the loading of counteractant and neutralizing agent in the web may be varied to achieve the desired odor management capabilities. For example, the range of Veilex™ counteractant agent may be from 0.05% to 5% (wt), or 500 ppm to 50,000;

likewise, the range of zinc ricinoleate neutralizing agent may be from 0.005% to 0.5% (wt), or 50 ppm to 5,000 ppm.

Web samples were tested for odor intensity using a modified version of ASTM E544-99. Web samples were ranked against a commercially available scented bag, Kitchen Fresh®, along with another commercial bag, Odor Shield®, and a commercial unscented bag, CinchSak®. The perceptible odor intensity ratings on a scale from 1-10 are listed in Table-1:

TABLE 1

Relative ratings of odor intensity of the web of the invention and commercial bags

|  | Odor Shield | Kitchen Fresh[1] | Cinch Sak | Samples of invention |
|---|---|---|---|---|
| Average rating | 6.8 | 5 | 1.0 | 1.3 |
| Std Error | 0.5 | (NA) | 0.3 | 0.4 |

[1]A reference sample with a rating of 5 to be used for relative ratings.

The results showed that the web samples having an odor management agent formulation of a cyclohexyl compound and a zinc ricinoleate compound are substantially free of fragrance so as to have no perceptible scent.

Bags were then made from the web of the invention for malodor reduction tests. The test was conducted by using a garbage mixture that contained ingredients that generated amines, aldehydes, marcaptans, ketones and ethers and that could be detected by gas chromatography mass spectroscopy (GCMS). The garbage mixture was developed by an independent sensory analysis consultant with a trained sensory panel. The garbage mixture was stored in the bag until a representative level of malodor was generated. The malodor intensity was determined by a sniff test conducted by the sensory consultant using a trained panel. On a scale from 1-10, the trained panel rated the standard, fragrance free bag as 7.6, and the invented bag having the odor management agent as 5.3, thus demonstrating that the bag of the invention no perceptible scent.

Further, the masterbatch that contained the same odor management agent formulation was used to produce the bags of the invention, which were then tested for odor reduction capabilities. The masterbatch was added at 2% (wt) to a matrix polymer of linear low density polyethylene to form a molten polymer mixture and then extruded through an extruder to make 0.9 mil thick blown oriented webs. Webs were tested for odor intensity by following the ASTM E544-99 method. Aqueous n-butanol solutions having concentrations ranging from 40 ppm to 4000 ppm were prepared in bottle and used for headspace sniff tests. A trained panel was assembled to conduct the sniff of the set of solutions that had serial changes of concentration and ratings were assigned. Various web samples of approximately 2"×6"×0.001" and weighed approximately 0.15 g were stored in 125-ml bottles and used for headspace odor intensity test. Web samples included commercially available bags Odor Shield®, a waste bag having a heavy fragrance; Kitchen Fresh®, a waste bag having a light fragrance; Cinch Sak®, a waste bag having no fragrance, and the web sample of the invention. The rating was ranked as equivalent ratings to n-butanol solutions. The odor intensity ranking was expressed as the equivalent n-butanol concentration. The results are shown in Table-2.

TABLE 2

Relative ratings of odor intensity of the web of the invention and commercial bags

|  | Odor Shield ® | Kitchen Fresh ® | Cinch Sak ® | Samples of invention |
|---|---|---|---|---|
| n-butanol, ppm | 1700 | 750 | 90 | 100 |

As defined herein, the n-butanol concentration for the unscented waste bag is preferably 300 ppm or less, more preferably 200 ppm or less, and most preferably 100 ppm or less. The equivalent loadings for the masterbatch used in the web is 4% (wt) or less, more preferably 3% (wt) or less. The range can be adjustable to fit the needs of intended product attributes. The example suggested that while the odor management agent formulation can be varied, the waste bag having the odor management agent incorporated therein should possess an odor intensity of 100 ppm equivalent n-butanol concentration or less as determined from this invention, so as to be substantially free or fragrance.

The test results showed that the samples of the instant invention having formulations of neutralizing agents comprising a zinc ricinoleate and a counteractant agent comprising a cyclohexyl compounds were substantially free of fragrance so as to have no perceptible scent, similar to that of an unscented web.

Web samples having 1% to 5% (wt) loading of odor management agent masterbatch were made by using the same blown film process and conditions. Samples were prepared for odor intensity measurement by using the ASTM E544-99 method described above. The headspace odor rating equivalent to the odor intensity of n-butanol concentration is shown in Table 3.

TABLE 3

Relative ratings of odor intensity for the effective additive formulations

|  | Masterbatch loading (wt %) | | | | |
|---|---|---|---|---|---|
|  | 1 | 2 | 3 | 4 | 5 |
| n-butanol, (ppm) | <100 | 100 | 100 | 300 | 600 |

The blown film equipment and processes can be any conventional set up that is capable of providing biaxial stretching or biaxial orientation for the chosen polymers. For the linear low density polyethylene (Dow Chemical, MI=0.9) used in this embodiment of invention, the typical orientation parameters are listed in Table 4.

TABLE 4

Blown film material orientation parameters used in the invention

|  | Typical Number | Range |
|---|---|---|
| Machine Direction Draw Ratio | 40 | 86-15 |
| Transverse Direction Draw Ratio | 2.5 | 1.5-4 |
| Area Draw Ratio | 100 | 60-129 |
| Die Wall Shear Rate (l/sec) | 102 | 10-200 |
| Film Thickness (mil) | 0.9 | 1.5-0.7 |

Webs with a single and two layer structure were produced by using a blown film extrusion device that has two extruders and 6" diameter annular die. The extruder and die temperature was set at 450° F. The extrusion output was approximately 200 lb/hr. For the single layer web, the masterbatch was mixed and melted with the matrix polymer resin to form a molten polymer mixture. The molten polymer mixture had the odor management agent distributed uniformly throughout in the web. For the two layer coextruded web, the masterbatch was distributed in the inner layer of the blown bubble with the inside/outside layer thickness ratio approximately 10/90 to 20/80.

Two different master batches were used in this test. One was from IFF (New York, N.Y.) and the other was from another supplier. The master batches contained the major ingredients as described in the invention. It was observed during the film blowing test that the two-layer coextruded web with the masterbatch in the inner layer provided two positive attributes: (1) low volatile evolution and smell in the environment; and (2) little or no die face build up.

Some mechanical properties were measured for the single and two layer coextruded web. When the masterbatch was coextruded in the inner layer, the web had a higher probe value of 55.8 in-lb/mil compared with 24.9 in-lb/mil for the single layer web, such that the lubricity of the film was improved.

While the disclosed web materials with active agent have been shown and described with reference to the illustrated embodiments, those of ordinary skill in the art will recognize and/or be able to ascertain many equivalents to those embodiments. Such equivalents are encompassed by the scope of the present disclosure and the appended claims.

For example, those of ordinary skill in the art will understand that the present invention has applications to various types of packages and containers, including non-reclosable bags and liners, rigid containers such as plastic containers, lunch containers, rigid trash containers, perishable packaging wraps and foils, such as food wraps and agricultural and/or industrial wraps and lidding materials or the like. Similarly, those of ordinary skill in the art will understand that the present invention has applications to active agents other than odor management agents, such as odor management agents and other agents providing a desired function or effect on a package or the contents disposed therein.

Unless otherwise provided, when the articles "a" or "an" are used herein to modify a noun, they can be understood to include one or more than one of the modified noun.

What is claimed is:

1. A bag having odor management capabilities, the bag comprising:
   a pair of opposing body panels joined together along a pair of opposing sides, and a bottom bridging the sides; and
   an odor management agent distributed in at least one of the body panels for release into an interior of the bag to substantially reduce malodors emanating from products disposed within the bag,
   wherein the odor management agent comprises a counteractant; and
   wherein the bag is substantially free of fragrance.

2. The bag of claim 1, wherein the counteractant is selected from the group consisting of 1-cyclohexyl-1-ethyl formate, 1-cyclohexyl-1-ethyl acetate, 1-cyclohexyl-1-ethyl proprionate, 1-cyclohexyl-1-ethyl isobutyrate, 1-cyclohexyl-1-ethyl n-butyrate, 1-cyclohexyl-1-propyl acetate, 1-cyclohexyl-1-propyl n-butyrate, 1-cyclohexyl-2-methyl-1-propyl acetate, 2-cyclohexyl-2-propyl acetate, 2-cyclohexyl-2-propyl propionate, 2-cyclohexyl-2-propyl isobutyrate, 2-cyclohexyl-2-propyl n-butyrate, 1-cyclohexylethan-1-yl acetate, 1-cyclohexylethan-1-yl butyrate, 1-cyclohexylethan-1-ol, 1-(4'-methylethyl)cyclohexylethan-1-yl propionate, 2'-hydroxyl-1'-ethyl(2-phenoxy)acetate.

3. The bag of claim 1, wherein the odor management agent is distributed substantially uniformly throughout the at least one of the body panels.

4. The bag of claim 1, wherein the odor management agent is activated by humidity or by contact with an aqueous solution or liquid.

5. The bag of claim 1, wherein the odor management agent is activated by contact with the products disposed within the bag.

6. The bag of claim 1, wherein the at least one body panel comprises a first layer and a second layer, the odor management agent distributed in one of the first layer and the second layer.

7. The bag of claim 1, wherein the at least one body panel comprises a first layer and a second layer, the odor management agent distributed in one of the first layer and the second layer, and the other of the first layer and second layer is a barrier material.

8. The bag of claim 1, wherein the at least one body panel comprises a first layer and a second layer, the odor management agent distributed in one of the first layer and the second layer, and the other of the first layer and second layer is a diffusion layer.

9. The bag of claim 1, wherein the odor management agent further comprises a neutralizing agent.

10. The bag of claim 9, wherein the neutralizing agent is selected from the group consisting of lauryl methacrylate, a biguanide, a quaternary ammonium compound, an ester of unsaturated monocarboxylic acid, an uncomplexed cyclodextrin, a zinc ricinoleate compound, and an alkoxylated amine having the formula $R(nAO)_s NH_t$, wherein R is a saturated or unsaturated, linear or branched alkyl containing from 8 to 22 carbon atoms, AO is a $C_2$-$C_6$ alkoxylate, n is the number of moles of AO and is from 1 to 50, s is 1, 2 or 3, t is 0, 1 or 2, and the sum of s and t is 3.

11. The bag of claim 10, wherein the neutralizing agent is a zinc ricinoleate compound.

12. The bag of claim 9, wherein the counteractant is loaded in the at least one of the body panels at about 0.05% to 5% (wt), and the neutralizing agent is loaded in the at least one of the body panel at about 0.005% to 0.5% (wt).

13. A bag having odor management capabilities, the bag comprising:
   a pair of opposing body panels joined together along a pair of opposing sides, and a bottom bridging the sides; and
   an odor management agent associated with at least one of the body panels for release into an interior of the bag to substantially reduce malodors emanating from products disposed within the bag,
   wherein the odor management agent comprises a counteractant and a neutralizing agent; and
   wherein the bag is substantially free of fragrance.

14. The bag of claim 13, wherein the association is by being distributed in at least one of the body panels for release into an interior of the bag.

* * * * *